(12) United States Patent
Gathergood et al.

(10) Patent No.: US 8,541,598 B2
(45) Date of Patent: Sep. 24, 2013

(54) BIODEGRADABLE SOLVENTS FOR THE CHEMICAL INDUSTRY

(75) Inventors: Nick Gathergood, Ashbourne (IE); Saibh Morrissey, Dublin (IE); Bruce Pegot, Joinville-le-Pont (FR)

(73) Assignee: Dublin City University, Dublin (IE)

( * ) Notice: Subject to any disclaimer, the term of this patent is extended or adjusted under 35 U.S.C. 154(b) by 636 days.

(21) Appl. No.: 12/673,200

(22) PCT Filed: Aug. 21, 2008

(86) PCT No.: PCT/EP2008/060978
§ 371 (c)(1), (2), (4) Date: Mar. 3, 2010

(87) PCT Pub. No.: WO2009/024607
PCT Pub. Date: Feb. 26, 2009

(65) Prior Publication Data
US 2011/0201824 A1    Aug. 18, 2011

(30) Foreign Application Priority Data
Aug. 21, 2007 (IE) .................................. 2007/0597

(51) Int. Cl.
*C07D 233/60* (2006.01)
*B01D 11/04* (2006.01)

(52) U.S. Cl.
USPC ................. 548/341.5; 548/341.1; 514/399

(58) Field of Classification Search
USPC ..................... 548/341.5; 514/399
See application file for complete search history.

(56) References Cited

U.S. PATENT DOCUMENTS

| | | | |
|---|---|---|---|
| 3,853,907 A * | 12/1974 | Edwards | 548/313.7 |
| 3,989,711 A | 11/1976 | Bodor | |
| 4,160,099 A | 7/1979 | Bodor | |
| 6,451,067 B1 | 9/2002 | Lagrange et al. | |
| 6,808,557 B2 | 10/2004 | Holbrey et al. | |

FOREIGN PATENT DOCUMENTS

| | | |
|---|---|---|
| EP | 0718288 | 6/1996 |
| GB | 1526819 | 10/1978 |
| JP | 54079278 | 6/1979 |
| WO | 0216367 | 2/2002 |
| WO | 03086605 | 10/2003 |
| WO | 2008082224 | 7/2008 |

OTHER PUBLICATIONS

Boxwell, et al., "A Highly selective arene hydrogenation catalyst that operates in ionic liquid," J. Am. Chem. Soc., 2002, vol. 124; p. 9334-9335.
Dupont, et al., "Transition-metal nanoparticles in imidazolium ionic liquids: recyclable catalysts fo biphasic hydrogenation reactions," J. Am. Chem. Soc., 2002, vol. 124; p. 4228-4229.
Dyson, et al., "A Comparison of Ruthenium-Catalysed Arene Hydrogenation Reactions in Water and 1-Alkyl-3-methylimidazolium Tetrafluoroborate Ionic Liquids," Adv. Synth. Catal. 2003; vol. 345, p. 216221.
Dyson, et al., "Determination of hydrogen concentration in ionic liquids and the effect (or lack of) on rates of hydrogenation," Chem. Commun. 2003; p. 2418-2419.
Rossi, et al., "On the use of ruthenium dioxide in 1-n-butyl-3-methylimidazolium ionic liquids as catalyst precursor for hydrogenation reactions," Catalysis Letters, 2004; vol. 92, Nos. 3-4; pp. 149-155.
Stefan, et al., "Selective Hydrogenation of Citral in an Organic Solvent, in a Ionic Liquid, and in Substance," Chem. Eng. Technol. 2007, vol. 30; p. 481-486.
Anderson, et al., "Heterogeneously catalysed selective hydrogenation reactions in ionic liquids," Green Chemistry. 2003, vol. 5; p. 448-453.
Zhao, et al., "Designing enzyme-compatible ionic liquids that can dissolve carbohydrates," Green Chem. 2008, vol. 10; pp. 696-705.
Yadav, et al., "Reactions on a Solid Surface. A Simple, Economical, and Efficient Acylation of Alcohols and Amines over Al2O3," J. Org. Chem. 2004, vol. 69; pp. 577-580.
APHA (American Pubic Health Association), AWWA (American Water Works Association), and WPCF (Water Pollution Control Federation), Method 508 B, Standard Methods for the Examination of Water and Wastewater, Washington, 16th edn, 1985; pp. 532-537.
Benvenuti, et al., "Hydrogenation of organic substrates by an heterogenized catalyst based on a bis (diphenylphosphino)methane polymer-bound palladium(II) complex," Journal of Molecular Catalysis A. 1999, vol. 145; p. 221-228.
Zhang, et al., "Catalytic selective hydrogenation of cinnamaldehyde to hydrocinnamaldehyde," Applied Catalysis A. 2000, vol. 192; p. 247-251.
Le Bras, et al., "Palladium nanoparticles obtained from palladium salts and tributylamine in molten tetrabutylammonium bromide: their use for hydrogenolysis-free hydrogenation of olefins," New J. Chem. 2004, vol. 28; p. 1550-1553.
Sajiki, et al., "Markedly chemoselective hydrogenation with retention of benzyl ester and N-Cbz functions using a heterogeneous Pd-fibroin catalyst," Tetrahedron Letters. 2003, vol. 44; p. 8437-8439.
Belotti, et al., "Hydrogenation versus hydrogenolysis with a safe, selective and reusable catalyst: palladium black on Teflons," New J. Chem. 2005, vol. 29; p. 761-764.
Monatshefte für Chemie. 2005, vol. 136, No. 10; pp. 1751-1755.

(Continued)

*Primary Examiner* — Kamal Saeed
*Assistant Examiner* — Janet L Coppins
(74) *Attorney, Agent, or Firm* — Fahmi Sellers Embert & Davitz

(57) ABSTRACT

This invention relates to ionic liquid (ILs) solvents for chemical synthesis based on an alkyl-imidazolium cation core containing ionic liquids which have enhanced biodegradability and reduced toxicity relative to existing imidazolium bases ILs such as 1-butyl-3-methylimidazolium (bmmim) salts. Many of the described ILs produce a score of over 60% biodegradability over 28 days in a biodegradability test such as the Sturm Test, the Closed Bottle Test (OECD 301D) or the $CO_2$ Headspace Test (ISO 14593). The ILs of the invention comprise an alkyl substituted imidazolium cationic core having a —C=OX— side chain in the 3-position of the imidazole ring, wherein X=O, NH, N or S and an associated counteranion characterized in that the —C=OX side chain comprises at least one ether linkage. The biodegradable and non-toxic IL may be used as green solvents for the chemical, pharmaceutical, biofuel and biomass industries. The ILs of the invention are particularly useful in hydrogenation, pericyclic and metathesis reactions.

31 Claims, 7 Drawing Sheets

(56) References Cited

OTHER PUBLICATIONS

Huang, et al. "A novel and efficient ionic liquid supported synthesis of oligosaccharides", Tetrahedron Letters, Elsevier, Amsterdam. May 1, 2006, vol. 47, No. 18; pp. 3047-3050.
Gathergood, et al. "Design and Preparation of Room—Temperature Ionic Liquids Containing Biodegradable Side Chains," Australian Journal of Chemistry. Jan. 1, 2002, vol. 55; pp. 557-560.
International Search Report for international application No. PCT/EP2008/060978 issued on Nov. 28, 2008.
Written Opinion for the International Application No. PCT/EP2008/060978 issued by the International Searching Authority mailed on Nov. 28, 2008.
Wasserscheid, et al., "Ionic Liquids—New 'Solutions' for Transition Metal Catalysis," Angew. Chem. Int. Ed. 2000, vol. 39; p. 3772-3789.
Welton, "Room-temperature ionic liquids. Solvents for synthesis and catalysis," Chem. Rev. 1999, vol. 99; p. 2071-2083.
Holbury et al., "Ionic liquids," Clean Prod. Process. 1999, vol. 1; p. 223.
Bonhote, et al., "Hydrophobic, highly conductive ambient temperature molten salts," Inorg. Chem. 1996, vol. 35; p. 1168-1178.
Swatloski, et al., "Dissolution of Cellose with Ionic Liquids," J. Am. Chem. Soc. 2002, vol. 124; pp. 4974-4975.
Phillips, et al., "Dissolution and regeneration of *Bombyx mori* silk fibroin via ionic liquids," J. Am. Chem. 2004, vol. 126; pp. 14350-14351.
Liu, et al., "Room-temperature ionic liquids that dissolve carbohydrates in high concentrations," Green Chem. 2005, vol. 7; pp. 39-42.
Xie, et al., "Ionic liquids as novel solvents for the dissolution and blending of wool keratin fibres," Green Chem. 2005, vol. 7; pp. 606-608.
Turner, et al., "Production of Bioactive Cellulose Films Reconstituted from Ionic Liquids," Biomacromolecules. 2004, vol. 5; pp. 1379-1384.
Turner, et al., "Ionic Liquid-Reconstituted Cellulose Composites as Solid Support Matrices for Biocatalyst Immobilization," Biomacromolecules. 2005, vol. 6; pp. 2497-2502.
Huddleston, et al., "Room Temperature Ionic Liquids as Novel Media for 'Clean' Liquid-Liquid Extraction," Chem. Commun. 1998; p. 1765-1766.
Blanchard, et al., "Green processing using ionic liquids and $CO_2$," Nature. May 6, 1999, vol. 399; pp. 28-29.
Visser, et al., "Traditional Extractants in Nontraditional Solvents: Groups 1 and 2 Extraction by Crown Ethers in Room-Temperature Ionic Liquids," Ind. Eng Chem. Res 2000, vol. 39; p. 3596-3604.
Hemeon, et al., "Manganese Dioxide Allylic and Benzylic Oxidation Reactions in Iionic Liquids," Aust. J. Chem. 2004, vol. 57, No. 2; pp. 125-128.
Sheldon, R., "Catalytic reactions in ionic liquids," Chem. Commun. 2001, vol. 23; p. 2399-2407.
Nelson, W. M., "Ionic liquids: industrial application for green chemistry," ACS Symp. 2002, Ser. 818, ed. R. D. Rogers and K. R. Seddon; pp. 30-41.
Laird, et al., "Some items of Interest to Process R&D Chemists and Engineers," Org. Process Res. Dev. 2002, vol. 6, No. 4; p. 338-345.
Swatloski, et al., "Ionic Liquids are not Always Green: Hydrolysis of 1-butyl-3-methylimidazolium Hexafluorophosphate," Green Chem. 2003, vol. 5; No. 4; p. 361-363.
Scott, et al., "The biodegradation of sur-factants in the environment," Biochim. Biophys. Acta. 2000, vol. 1508, Nos. 1-2; p. 235.
Freer, et al., "The Pros and cons of using ionic liquids in the pharmaceutical industry," NATO Sci. Ser. II: Math. Phys. Chem. 2003, vol. 92; p. 129-136.
Holbrey, J. D., "Ionic liquids: industrial applications for green chemistry," ACS Symp. 2002, Ser. 818, ed. R. D. Rogers and K. R. Seddon; pp. 2-4.
Seddon, K. R., "In this efficient case methyl imidazole is converted to the ionic liquid (the hydrochloride salt of methyl imidazole), then the methyl imidazole is regenerated and recycled," Nat. Mater. 2003, vol. 2, No. 6; p. 363-365.
Bodor, et al., "Soft drugs 1. Labile quaternary ammonium salts as soft antimicrobials," J. Med. Chem. 1980, vol. 23, No. 5; p. 469-474.
Bodor, et al., "Soft drugs 2. Soft alkylating compounds as potential antitumor agents," J. Med. Chem. 1980, vol. 23, No. 5; p. 566.
Zhao, et al., "On the catalytic activity of cluster anions in styrene hydrogenation: considerable enhancements in ionic liquids compared to molecular solvents," Journal of Molecular Catalysis A, 2004, vol. 214; p. 19-25.
Boethling, R. S., "Designing Safer Chemicals," ACS Symp. 1996, Ser. 640; p. 156.
Howard, et al., "Development of a predictive model for biodegradability based on BIODEG, the evaluated biodegradation data base," Sci. Total Environ. 1991, vol. 109/110; p. 635-641.
Boethling, R. S., "Cationic Surfactants," Surfactant Science Series. 1994, vol. 53; pp. 95-135.
Gathergood, et al., "Design and Preparation of Room-Temperature Ionic Liquids Containing Biodegradable Side Chains," Aust. J. Chem. 2002, vol. 55; pp. 557-560.
Gathergood, et al., "Bio-degradable Ionic Liquids: Part I. Concept, Preliminary Targets and Evaluation," Green Chemistry. 2004; pp. 166-175.
Garcia, et al., "Bio-degradable Ionic Liquids: Part II. Effect of the Anion and Toxicology," Green Chemistry. 2005; pp. 9-14.
Gathergood, et al., "Bio-degradable Ionic Liquids: Part III. The First Readily Bio-degradable Ionic Liquids," Green Chemistry. 2006; pp. 156-160.
Jastorff, et al. "How hazardous are ionic liquids? Structure activity relationships and biological testing as important elements for sustainability evaluation," Green Chem. 2003, vol. 5; p. 136-142.
OECD Chemical Group, Ready Biodegradability: Closed Bottle Test. Method 301 D, OECD Revised Guidelines for Tests for Ready Biodegradability, Paris, France, 1993.
ISO 14593: Water quaiity. Evaluation of ultimate aerobic biodegradability of organic compounds in aqueous medium. Method by analysis of inorganic carbon in sealed vessels ($CO_2$ headspace test), 1999.
Kume, et al., Catalysis Communications. 2008, vol. 9; p. 369.
Kanazawa, et al., "Conjugate reduction of alpha,beta-unsaturated aldehydes with rhodium(bis-oxazolinylphenyl) catalysts," Synlett. 2006, vol. 19; p. 3343-3345.
Lopez-Linares, et al., "Regioselective hydrogenation of olefinic or carbonyl functional group of alpha,beta-unsaturated substrates by iridium cyclocta-1,5-diene precursor stabilized with hydro(pyrazolyl)borate ligands," Journal of Molecular Catalysis A. 2004, vol. 207; p. 115-122.
Mori, et al., "Chemoselective hydrogenation method catalyzed by Pd/C using diphenylsulfide as a reasonable catalyst poison," Tetrahedron, 2006, vol. 62; p. 11925-11932.
Ikawa, et al., "Highly chemoselective hydrogenation method using novel finely dispersed palladium catalyst on silk-fibroin: its preparation and activity," Tetrahedron, 2005, vol. 61; p. 2217-2231.
Wolfson, et al., "Beneficial effect of water as second solvent in ionic liquid biphasic catalytic hydrogenations," Tetrahedron Letters, 2005, vol. 46; p. 2513-2516.
Suarez, et al., "Two-phase catalytic hydrogenation of olefins by Ru(II) and Co(II) complexes dissolved in 1-n-butyl-3-methylimidazolium tetrafluoroborate ionic liquid," Inorganica Chimica Acta, 1997, vol. 255; p. 207-209.
Suarez, et al., "Catalytic Hydrogenation of 1-hexene with $RuCl_2(TPPMS)_3(DMSO)$, Part II: Ionic liquid biphasic system," React. Kinet. Catal. Lett., 2004, vol. 82; p. 325-331.
In Hydrogenation Methods (Best Synthetic Methods), London; Orlando [Fla.]: Academic Press, 1985; Paul Neis Rylander; p. 165.

\* cited by examiner

6

KG 20

KG 20

KG 15

BIODEGRADABLE SOLVENTS FOR THE CHEMICAL INDUSTRY

FIELD OF THE INVENTION

This invention relates to the provision of biodegradable solvents for the chemical industry. More particularly, the invention relates to the provision new ionic liquids (ILs) for use as solvents for reactions such as chemical synthesis and biomass dissolution. More particularly still, the ionic solvents of the invention are based on ionic liquids containing an alkyl-imidazolium cation core that have enhanced biodegradability and reduced toxicity relative to existing imidazolium-based ILs such as 1-butyl-3-methylimidazolium (bmim) salts.

BACKGROUND TO THE INVENTION

Ionic liquids (ILs) have been the subject of considerable interest as media for a wide range of synthetic and analytical processes.(1, 2) They are considered in a 'green chemistry' context due to their low vapour pressure, ease of recovery facilitating recycling (3) and applicability to catalytic processes.(4) ILs are characterized by a melting point below 100° C. ILs possess a number of interesting properties such as high polarity and ionic conductivity, a wide window of electrochemical potential and excellent chemical and thermal stability to a wide range of chemicals even at high temperatures. However, it is this stability that has led to questions as to the potential for ILs to accumulate in the environment over time.(5) Ionic liquids may cause problems either from premature degradation or environmental persistence, with the result that when the ionic liquid has served its operational use, disposal becomes an issue. As the pressure to reduce incineration and landfill waste increases, so the requirement for chemicals which are biodegradable also increases.(6) Within the field of green chemistry it is unacceptable to produce large quantities of waste which have high ecotoxicity or biological activity.(7) Seddon reported the first industrial process where ionic liquids were used on a multi-tonne scale.(8) As ionic liquids advance from academic curiosities the need to consider their toxicity and biodegradation is paramount before processes using ionic liquids are scaled up.

Although there has been intense interest in the use of ionic liquids (ILs) (FIG. 1) as green solvents, relatively little is known about their biodegradability and toxicity, which are basic properties in the environmental risk assessment of any organic compound.

The biodegradability of the ILs can be evaluated applying the following standard methods: (i) Sturm Test (ii) Closed Bottle Test (OECD 301D) (iii) $CO_2$ Headspace Test (ISO 14593). Both tests (ii) and (iii) are included in the European Regulation (EC) No 648/2004 of biodegradability of detergent surfactants, the $CO_2$ Headspace Test being the reference method for laboratory testing of ultimate biodegradability. In the Closed Bottle and $CO_2$ Headspace tests, the compound to be evaluated is added to an aerobic aqueous medium inoculated with wastewater microorganisms and the depletion of dissolved $O_2$ or the $CO_2$ evolution is measured periodically and reported as a percentage of theoretical maximum. Sodium n-dodecyl sulfate (SDS) is generally used as a reference substance.

An IL will be considered "readily biodegradable" and, therefore it will be assumed that such a chemical will be rapidly and completely biodegraded in an aquatic environment under aerobic conditions, if the biodegradation level measured according to one of the described tests is higher than 60% within 28 days.

IL toxicity tests are based on systems with different biological complexity levels. The toxicity of the ILs has been measured on a wide range of organisms from bacteria and fungi, to higher organisms such as zebrafish, the soil nematode and the freshwater snail. LC50, IC50, EC50 and MIC values are used as a measurement of the toxicity of the ILs on the organism. Growth inhibition studies have also been carried out on algae and terrestrial plants. Such tests indicate the levels at which the IL in a biological system prevents or disrupts growth. Data from such studies on ILs can then be compared to well known values for common organic solvents. In general the toxicity of ionic liquids tested to date is found to be some orders of magnitude higher than that of conventional solvents such as acetone and methanol. A common problem with the toxicity of ionic liquids is associated with the presence of an extended hydrocarbon chain. The length of the side chains was found to influence the dialkylimidazolium ionic liquid's toxicity, with longer chain length proving to be more toxic. In fact, Bodor et al. (9) have shown that the long chain ester derivatives of methyl imidazole (shown as compound 6 in FIG. 3) show effective antimicrobial activity at ppm concentrations, clearly demonstrating the toxic effect of such ILs on microbes.

In 1991, Howard et al, (10) published a report on the development of a model for predicting aerobic biodegradability of organic compounds based on chemical structure alone. Organic compounds having certain structural fragments known or thought to have an impact on biodegradability were examined, e.g., addition of an ester functional group is known to generally increase biodegradability. Excellent predictive results for many of the compounds were achieved. However, interestingly, certain compounds, include certain aliphatic ethers were incorrectly predicted to biodegrade quickly.

In 1996, Boethling reported that over 40 years of studies had shown that relatively small changes in molecular structure can appreciably alter a chemical's susceptibility to biodegradation. Such studies have resulted in several "rules of thumb" about effects of chemical structure on biodegradability. These rules included that molecular features such as e.g., halogens, chain branching, nitro groups, heterocyclic residues and aliphatic ethers all generally lead to increased resistance to aerobic biodegradability (10).

In 2002, Gathergood and Scammells conducted the first study of IL biodegradability, based on investigations into effects of substituents on the biodegradability of ILs containing a dialkylimidazolium cation (11). (FIG. 1) Nitrogen-containing heterocycles were already known to be difficult groups for degradation by microorganisms (9). Gathergood and Scammells found that the combination of features of an imidazolium cation core, an anion such as $Br^-$, $BF_4^-$, $PF_6^-$, $NTf_2^-$ or $N(CN)_2^-$, and an unsubstituted linear alkyl ester or alkyl amide side chain (ethyl-octyl) furnished ILs which were for the most part, liquid at room temperature. A limited number of these compounds were shown to evolve $CO_2$ in the region of 48-60% when subjected to the Sturm biodegradability test (ISO9439: a pass being 60% evolution, 80% evolution deemed "readily biodegradable").

In 2004, Gathergood, Scammells and Garcia (11) produced imidazolium ILs using standard methods for imidazolium ILs which involved alkylation of methyl imidazole with the appropriate alkyl esters or amide derivates of bromoacetic acid. Counterion exchange procedures allowed introduction of alternative counterions and formation of the ILs in good yield. Biodegradability was assessed using the "Closed Bottle Test" (OECD 301D) against sodium dodecyl sulfate as reference wherein a biodegradability result greater than 60% for tested compounds means the compound is deemed "readily biodegradable". Gathergood and Garcia reported that the commonly used dialkylimidazolium ILs (BmimX) showed negligible biodegradability (in the range of 0-2% degradation over 28 days) in the Closed Bottle Test. However, the incorporation of an ester in the side chain of the imidazolium cation significantly increased biodegradability over BmimXs, whereas incorporation of an amide in the side chain showed a far lesser biodegradability effect, however the results still fell far short of 60% biodegradability within 28 days. 3-Methyl-1-(pentoxycarbonylmethyl) imidazolium bromide proved to be the most biodegradable compound in this series, giving a result of just 32% degradation after 28 days. Gathergood and Garcia also showed that the biodegradability increased slightly with increasing alkyl side chain length for the lowest alkyl esters and later remained relatively constant, with ester of chain length greater than 4 proving to be the most biodegradable. It was postulated that enzymatic cleavage of the ester bond led to easily metabolized fragments. In this paper the authors briefly identified the negative effect compound toxicity may have on biodegradability, since many quaternary ammonium salts are known to be potential biocides and so a discussion was presented that certain ILs may inhibit the growth of biodegrading microorganisms. Clearly, it is desirable to produce ILs that are less toxic to biodegrading microorganisms.

Other groups have examined IL toxicology (12) and it has been found that the length of alkyl chain affects the biological properties of such molecules, with longer alkyl chains associated with higher toxicity. As previously mentioned, one particular compound containing an ester group in the side chain of an imidazolium salt has a clear-cut toxic effect and indeed has been shown to be a potent antibacterial (9) (see FIG. 3 for a structural comparison). In this case Bodor designed the chemical as part of a medicinal chemistry project to make use of the biological activity of this class of compounds.

Later in 2004, Gathergood, Scammells and Garcia (11) looked at the effect of the counter anion and the alkyl chain length on biodegradability and toxicology of the imidazolium based ILs as compared to BmimBr analogues. Counter anions such as $Br^-$, $BF_4^-$, $PF_6^-$, $NTf_2^-$, $N(CN)_2^-$ and $octylOSO_3^-$ were examined. An IL comprising an octylsulfate anion and alkyl ester side chain showed the highest biodegradability according to the Closed Bottle Test (49% biodegradation after 28 days) as compared to commonly used ILs, $BmimBF_4$ and $BmimPF_6$, which proved to be poorly biodegradable.

However, it must be noted that none of the disclosed compounds in any of these studies could be classified as "readily biodegradable". Bioassay aquatic toxicity tests on freshwater crustacea and saltwater bacteria showed that toxicity of the tested ILs became more pronounced with increasing alkyl chain length. Toxicity was far more pronounced than with organic solvents such as acetone, acetonitrile and even chlorinated solvents, yet lower than for cationic surfactants. It was also shown that as the chain length increases, the difference in toxicity between the ILs and cationic surfactants decreases significantly. It was proposed that the crucial factor in relation to aquatic toxicity was the length of the alkyl side chain, the inorganic counter anion having only a small effect.

More recently still, Gathergood, Scammells and Garcia reported the first ILs which were classifiable as "readily biodegradable" under aerobic conditions using the "Closed Bottle Test" (OECD 301D) and the "$CO_2$ Headspace Test" (ISO 14593) (11, 13, 14). Furthermore, investigations were directed to the nature of the effect of the addition of a 2-methyl group to the imidazole unit of the IL. 2-Methyl substitution was considered to have potential benefits in increasing biodegradability, since the addition of such an electron donating group should activate the ring to attack, and also should overcome the tendency of ILs containing an imidazole ring to form carbenes, where carbene formation is undesirable. 1-Alkoxycarbonyl-3-methylimidazolium cations and 1-alkoxycarbonyl-2,3-dimethylimidazolium analogues were tested. Surprisingly, the addition of the 2-methyl group to the IL had no significant effect on the biodegradation results. Interestingly, the $CO_2$ Headspace Test data were consistent with the Closed Bottle Test and in fact, provided biodegradability results in the range 60-67% for particular ILs containing both an ester group in the side chain and octylsulfate as counter ion. The higher results compared to those of the Closed Bottle Tests are thought to be related to differences in the cell density of the tests. The results allow a family of ILs to be classified as "readily biodegradable" for the first time, in other words it can be assumed that the particular ILs will be rapidly mineralised/biodegraded in aquatic environments under aerobic conditions. Finally, the possibility of an inhibitory effect of BmimX compounds on aerobic microorganisms was investigated and no toxic effect was shown at the test concentrations. The concentrations screened for antibacterial activity are generally from 2 μg/ml to 1000 μg/ml. Potent antibacterials will have MIC values at the lower end of this range, while compounds which have MIC values at the higher end of the range, show antibacterial activity but not at levels significant for antibacterial drug development. IL compounds displaying a lack antibacterial activity at levels of up to 20000 μg/ml, would be most desirable. At these high concentrations a lack of antibacterial activity would be a significant result.

Green solvents find one use in the field of transition metal catalysis, where one of the principal present day difficulties is the inefficient recycling and reuse of costly catalysts and ligands. Where economically efficient catalysts are used, selectivity is usually poor and elaborate poisons or conditions are needed to improve the result (15). Due to the physico-chemical properties of ILs, compared with those of organic and aqueous media, they provide a means of catalyst immobilization (16). The non-nucleophilic nature bestows an inert reaction medium that can also provide an extension of the catalyst lifetime (17). Low-polarity compounds, for example diethyl ether and n-hexane, are commonly insoluble in ILs. This varying solubility of the aforementioned organic solvents and ILs provides a suitable environment for biphasic catalysis. The positive aspects of homogeneous and heterogeneous catalysis are combined using a biphasic system. In this phase system, the catalyst resides in the IL and the substrates/products reside in the alternate phase. This system can implement a cost-effective way to successfully separate the desired product by simple decantation, leaving the catalyst immobilised in the IL, equipped for reuse. In the case of monophase catalysis in ILs, where the substrates are soluble in the IL medium, simple extraction or indeed facile distillation, due to the low vapour pressure of the IL, can be utilised as an alternative method for separating products from the IL/catalyst system.

Many common ILs have been investigated as alternative solvents for catalytic hydrogenations. Of these studies, the greater part focuses on the common commercially available ILs of the form $RMim^+$ (R: alkyl chain) $X^-$ (18). (FIG. 1)

Palladium on Carbon is well known as a universal catalyst for olefin hydrogenation, however its efficient catalytic activity may lead to poor selectivity. Thus it is desirable to provide alternative green solvents which may be used in organic reactions, such as hydrogenation reactions for example. Of particular interest are such solvents which may be used in hydrogenation of compounds such as trans-cinnamaldehyde or benzyl cinnamate using the commercially available Pd/C catalyst and which will allow superior control of the conversion and selectivity.

Thus, it is desired to assist in the development of green methods for drug manufacture in the chemical industry through the provision of a series of "readily biodegradable" ionic liquid solvents (ILs) for use in chemical synthesis which are non-toxic or show a reduced toxicity when compared to more traditional ionic liquid solvents. Such biodegradable and non-toxic ionic liquid solvents are highly desirable since producing less waste leads to cost savings in disposal, and a more environmentally friendly profile for the company.

It is desirable to combine desirable solvent properties such biodegradability and coordination ability in a solvent that can be tailored to the specific needs of a reactions, for example, enhanced conversion and/or selectivity of product. The ionic liquids in the present invention allow such solvent tailoring.

Further desirable is the provision of a designer library of ionic liquid solvents that possess these characteristics and yet are economically viable, robust and ideally suited to the preparation of drugs. The ionic liquids of the invention yield an excellent commercial source for tunable achiral coordinating, biodegradable and non-toxic solvents.

Furthermore, ionic liquids have been recognized as important solvents for biomass dissolution, because in most cases conventional liquids are incapable of dissolving a variety of important biomolecules, including biopolymers such as cellulose, silk, wool and other forms of keratin (1). Smaller carbohydrate oligomers as well as polymeric carbohydrates can also be solubilised by appropriate ionic liquid (1). It is highly desirable therefore to use non-toxic and/or biodegradable ionic liquids for biomass dissolution.

SUMMARY OF THE INVENTION

According to the present invention, as set out in the appended claims, there is provided a compound comprising an alkyl substituted imidazolium cationic core having a —C═OX— side chain in the 3-position of the imidazole ring, wherein X═O, NH, N or S and an associated counter anion, characterised in that the —C═OX— side chain comprises at least one ether linkage. Thus, the invention provides a series of compounds which can be used as ionic liquids for numerous chemical reactions. The compounds of the invention thus comprise an alkyl substituted imidazolium cationic core having an ester, amide or thioester (—C═OX—; wherein X═O, NH, N or S respectively) side chain in the 3-position of the imidazole ring and an associated counter anion wherein the ester, amide or thioester side chain comprises at least one ether linkage. Many of the ionic liquid compounds of the present invention have a biodegradability of at least 60% over 28 days duration when subjected to standard biodegradability testing (such as the $CO_2$ Headspace Test data or the Closed Bottle Test), and a reduced toxicity when compared with other compounds used as ionic liquids to date. Surprisingly, and contrary to well established biodegradability rules of thumb briefly discussed earlier, such ether or poly ether containing side chains produce IL compounds having greatly reduced toxicity and increased biodegradability when compared to previous ILs.

The ILs of the invention have an ester side chain, an amide or a thioester side chain which comprises an extended chain, the chain further comprising at least one ether linkage. In particular, side chains having from 4 to 13 atoms in the chain are preferred, however side chains having from 6 to 10 atoms are more particularly preferred.

In one embodiment, X may be O and the —C═OX— group represents a functional group side chain comprising an ester group.

In a different embodiment, X may be S such that the —C═OX— group represents a functional group side chain comprising a thioester group.

In yet another embodiment, wherein X may be N or $NHR_1$ or $NR_1R_2$, the —C═OX— group represents a functional group side chain comprising an amide. The amide group may be a secondary amide or a tertiary amide. When the —C═ON— group is a tertiary amide of the formula —$CONR_1R_2$, $R_1$ and $R_2$ may be a $C_1$-$C_{13}$ alkyl group (from 1 to 13 atoms in chain), wherein $R_1$ and $R_2$ may be the same or different, and at least one of $R_1$ and $R_2$ may comprise at least one ether linkage. Where $R_1$ and $R_2$ are different, one of $R_1$ and $R_2$, not containing an ether linkage may comprise a $C_1$-$C_4$ alkyl group; or $R_1$ and $R_2$ may together form a heterocyclic ring having 5 to 7 atoms wherein the ring may comprise at least one other heteroatom in addition to the amide nitrogen. Preferably, said heterocyclic ring comprises 6 atoms in the ring. It is preferable that the ring comprises at least one oxygen atom.

When the —C═ON— group is a secondary amide group ($CONHR_1$), $R_1$ may have from 4 to 13 atoms in the side chain. When the —C═ON— group is a tertiary amide group (—$CONR_1R_2$), $R_1$ and $R_2$ each may have from 1 to 13 atoms in the chain, wherein both $R_1$ and $R_2$ groups may be the same or different and may comprise from 1 to 3 ether linkages in each of the $R_1$ and $R_2$ chains. In a particular embodiment, where one of either $R_1$ or $R_2$ contains ether linkages, the other R may be a $C_1$-$C_4$ alkyl group. When the —C═ON— group is a tertiary amide functional group, it may comprise the nitrogen of the amide group as part of a heterocyclic ring, wherein the ring may contain at least one ether oxygen. The amide may be either a cisoid or transoid rotamer, or any combination of the two rotamers.

Used herein, an alkyl group is any of a series of univalent groups of the general formula $C_nH_{2n+1}$ derived from aliphatic hydrocarbons. Alkyl chains can be straight or branched. The methyl group (—$CH_3$) represents a $C_1$ alkyl group, ethyl (—$C_2H_5$) represents a $C_2$ alkyl group, nonyl group represents a $C_9$ alkyl group, dodecyl group represents a $C_{12}$ group etc.

An ether group has an oxygen atom connected to two (substituted) alkyl groups (general formula R—O—R'). A typical example is ethoxyethane ($CH_3$—$CH_2$—O—$CH_2$—$CH_3$).

Herein, when the alkyl group comprises at least one ether linkage, this means that at least one carbon (—HCH—) in the alkyl chain is substituted by at least one oxygen (—O—) to give an alkyl chain containing at least one ether linkage. The number of carbon atoms substituted by oxygen depends on the number of ether links required in the chain.

The compounds of the invention have imidazolium cores which may be substituted around the imidazolium ring by at least one $C_1$-$C_4$ alkyl substituents or by at least one halogenated alkyl substituents. Suitably, the alkyl substituted imidazolium core may possess a $C_1$-$C_4$ alkyl substituent at the 1-position of the imidazolium core. However, $C_1$-$C_2$ alkyl substituents at the 1-position are the preferred substituents. The most favoured substituents are methyl substituents at the 1-position. It is also possible to have further substituents on the imidazolium ring, such further substituent may be at least one $C_1$-$C_4$ alkyl substituent or at least one halogenated alkyl substituent, such as trifluoromethyl. Thus, the compounds of the invention comprise IL compounds having an alkyl substituted imidazole ring which may be substituted in at least one position with an alkyl group selected from the group consisting of 1-methyl, 2-methyl, 4-methyl, 5-methyl, 1-ethyl, 2-ethyl, 4-ethyl, 5-ethyl, 1-propyl, 2-propyl, 4-propyl, 5-propyl and 4-trifluoromethyl. However, the most preferred compounds of the invention comprise a 1-methyl substituent on the imidazolium core.

In all of the embodiments described, for all of the compounds, the —C=OX— group side chain may comprise from 1 to 4 ether linkages. Thus, the compounds of the invention may comprise an ester, amide or thioester side chain at the 3-position of the imidazole ring, which may have at least one ether linkage in the side chain. However, it is preferable that the ester or amide or thioester side chains contain polyether linkages. Preferably, the —C=OX— side chain comprises from 1 to 4 ether linkages. Particularly preferred are ILs of the invention having side chains comprising from 2 to 4 ether linkages, most preferred are ILs having side chains comprising 2 to 3 ether linkages.

Suitably, the compounds of the invention may comprise an ether or polyether linkage containing an ester side chain which may be selected from the group consisting of 2-methoxyethyl ester, 2-ethoxyethyl ester, 2-propoxyethyl ester, 2-butoxyethyl ester, 2-(2-ethoxyethoxy)ethyl ester, 2-(2-propoxyethoxy)ethyl ester and 2-(2-butoxyethoxy)ethyl ester, 2-[2-(2-methoxyethoxy)ethoxy]ethyl ester, 2-[2-(2-ethoxyethoxy)ethoxy]ethyl ester, 2-[2-(2-propoxyethoxy)ethoxy]ethyl ester and 2-[2-(2-butoxyethoxy)ethoxy]ethyl ester.

Suitably, other compounds of the invention may comprise an ether or polyether linkage containing an amide side chain which may be selected from the group consisting of 2-methoxyethyl amide, 2-ethoxyethyl amide, 2-propoxyethyl amide, 2-butoxyethyl amide, 2-(2-methoxyethoxy)ethyl amide, 2-(2-ethoxyethoxy)ethyl amide, 2-(2-propoxyethoxy)ethyl amide and 2-(2-butoxyethoxy)ethyl amide, 2-[2-(2-methoxyethoxy)ethoxy]ethyl amide, 2-[2-(2-ethoxyethoxy)ethoxy]ethyl amide, 2-[2-(2-propoxyethoxy)ethoxy]ethyl amide, 2-[2-(2-butoxyethoxy)ethoxy]ethyl amide, bis-(2-methoxyethyl) amide and N,N-2-methoxyethyl-2-propoxyethyl amide. The invention includes bis substituted amide examples of the above amide substituents (for example, but not restricted to bis-(2-methoxyethyl) amide) and unsymmetrically substituted amide derivatives (for example, but not restricted to N,N-2-methoxyethyl-2-propoxyethyl amide).

In an alternative embodiment, the compounds of the invention may comprise a tertiary amide side chain comprising cyclic ethers, such as the morpholine group for example.

In a different embodiment, the compounds of the invention may comprise an ether or polyether linkage containing a thioester side chain, wherein the —C=OS— side chain may be selected from the group consisting of 2-methoxyethyl thioester, 2-ethoxyethyl thioester, 2-propoxyethyl thioester, 2-butoxyethyl thioester, 2-(2-ethoxyethoxy)ethyl thioester, 2-(2-propoxyethoxy)ethyl thioester and 2-(2-butoxyethoxy)ethyl thioester, 2-[2-(2-methoxyethoxy)ethoxy]ethyl thioester, 2-[2-(2-ethoxyethoxy)ethoxy]ethyl thioester, 2-[2-(2-propoxyethoxy)ethoxy]ethyl thioester and 2-[2-(2-butoxyethoxy)ethoxy]ethyl thioester.

With respect to all embodiments described thus far, the compounds of the present invention comprise a counter anion which may be selected from the group consisting of $Br^-$, $Cl^-$, $NTf_2^-$, $PF_6^-$, $N(CN)_2^-$, sulfate, $OctOSO_3^-$, tosylate, benzenesulfonate, hydrogen sulfate, a linear alkyl sulfate, heptadecafluorooctanesulfonate, 2-(2-methoxyethoxy)-ethylsulfate, methanesulfonate, trifluoromethanesulfonate, nonafluorobutanesulfonate, phosphate, dimethyl phosphate, diethyl phosphate, bis(pentafluoroethyl)phosphinate, bis(2,4,4-trimethylpentyl)-phosphinate, tris(pentafluoroethyl)trifluorophosphate, tris(heptafluoropropyl)trifluorophosphate, tris(nonafluorobutyl)trifluorophosphate, diethylphosphate, nitrate, thiocyanate, tricyanomethanide, bis(pentafluoroethylsulfonyl)imide, bis(trifluoromethyl)imide, tris(trifluoromethylsulfonyl)methide, bis(methanesulfonyl)amide, 2,2,2-trifluoro-N-(trifluoromethylsulfonyl)acetamide and tetracyanoborate, bis[oxalato]borate, bis-[1,2-benzenediolato(2-)]borate, bis-[salicylato(2-)]borate, bis-[malonato(2-)]-borate, bis-[2,2'biphenyl-diolato-(2-)-O,O']-borate, acetate, trifluoroacetate, decanoate, hexafluoroantimonate, tetrachloroaluminate and cobalt tetracarbonyl. For the embodiments comprising a linear alkyl sulfate anion, the linear alkyl sulfate may have a general formula $C_nH_{2n+1}OSO_3^-$, wherein n=1 to 8. For example, the linear alkyl sulfate may be selected from the group consisting of methyl sulfate, ethyl sulfate, propyl sulfate, butyl sulfate, pentyl sulfate, hexyl sulfate, heptyl sulfate or trifluoroethyl sulfate.

The most preferred IL compounds of the invention comprise a $Br^-$, $NTf_2^-$, $BF_4^-$, $PF_6^-$, $N(CN)_2^-$, $OctOSO_3^-$, $Cl^-$ or $I^-$ counteranions. However, IL compounds having the $OctOSO_3^-$ anion are the most preferred ILs, since use of the $OctOSO_3^-$ anion provides the most biodegradable ionic liquids.

The biodegradability of the imidazole based ionic liquid compounds of the invention which comprise said ether or polyether linkage containing ester side chains, is not significantly decreased by replacing a bromide counter anion with a counter anion which is selected from the group consisting of $NTf_2^-$, $BF_4^-$, $PF_6^-$, $N(CN)_2^-$, $OctOSO_3^-$, $Cl^-$ and $I^-$. The introduction of any of these counteranions to the ILs of the invention has advantage of reducing the toxicity of the imidazole based ionic liquids when compared to traditional ionic liquid solvents (e.g. $bmimBF_4$ and $bmimPF_6$).

In a related embodiment, there is provided a method of preparing the IL compounds of the invention comprising the steps of:
  (i) forming a halo ester alkylating agent by reacting an alcohol comprising an ether or polyether group with halo acetyl halide; and
  reacting said halo ester alkylating agent with an imidazole to form an imidazole ester halide salt; or
  (ii) forming a halo thioester alkylating agent by reacting a thiol comprising an ether or polyether group with halo acetyl halide; and
  reacting said halo thioester alkylating agent with an imidazole to form an imidazole thioester halide salt; or
  (iii) forming a halo amide alkylating agent by reacting an amide comprising an ether or polyether group with halo acetyl halide; and
  reacting the halo amide alkylating agent with an imidazole to form an imidazole amide halide salt.

The halo acetyl halide may be selected from the group consisting of bromo acetyl bromide, chloro acetyl chloride, bromo acetyl chloride and chloro acetyl bromide. Preferably, the halo acetyl halide is bromo acetyl bromide.

The properties of ionic liquid compounds formed by this method can be altered by way of a further synthetic step that involves reacting the imidazole ester halide salt with a suitable alkali salt in an anion exchange reaction. It is preferable that the alkali salt comprises an $NTf_2^-$, $BF_4^-$, $PF_6^-$, $N(CN)_2^-$ or $OctOSO_3^-$ anion. Suitably, such alkali salts include, but are not limited to $LiNTf_2$, $NaBF_4$, $KPF_6$, $NaN(CN)_2$, Na $OctOSO_3$. The person skilled in the art will appreciate that many other alkali salts may be suitably used including the counteranions mentioned above.

In any of the methods of the invention, the halo ester alkylating agent may be selected from 2-methoxyethyl ester, 2-ethoxyethyl ester, 2-propoxyethyl ester, 2-butoxyethyl ester, 2-(2-ethoxyethoxy)ethyl ester, 2-(2-propoxyethoxy) ethyl ester and 2-(2-butoxyethoxy)ethyl ester, 2-[2-(2-methoxyethoxy)ethoxy]ethyl ester, 2-[2-(2-ethoxyethoxy)ethoxy] ethyl ester, 2-[2-(2-propoxyethoxy)ethoxy]ethyl ester, 2-[2-(2-butoxyethoxy)ethoxy]ethyl ester.

Alternatively, the ether or polyether linkage containing halo amide alkylating agent may be selected from the group consisting of 2-methoxyethyl amide, 2-ethoxyethyl amide, 2-propoxyethyl amide, 2-butoxyethyl amide, 2-(2-methoxyethoxy)ethyl amide, 2-(2-ethoxyethoxy)ethyl amide, 2-(2-propoxyethoxy)ethyl amide and 2-(2-butoxyethoxy)ethyl amide, 2-[2-(2-methoxyethoxy)ethoxy]ethyl amide, 2-[2-(2-ethoxyethoxy)ethoxy]ethyl amide, 2-[2-(2-propoxyethoxy) ethoxy]ethyl amide, 2-[2-(2-butoxyethoxy)ethoxy]ethyl amide, bis-(2-methoxyethyl) amide and N,N-2-methoxyethyl-2-propoxyethyl amide.

In another related embodiment, the ether or polyether linkage containing halothioester alkylating agent may be selected from the group consisting of 2-methoxyethyl thioester, 2-ethoxyethyl thioester, 2-propoxyethyl thioester, 2-butoxyethyl thioester, 2-(2-ethoxyethoxy)ethyl thioester, 2-(2-propoxyethoxy)ethyl thioester and 2-(2-butoxyethoxy)ethyl thioester, 2-[2-(2-methoxyethoxy)ethoxy]ethyl thioester, 2-[2-(2-ethoxyethoxy)ethoxy]ethyl thioester, 2-[2-(2-propoxyethoxy)ethoxy]ethyl thioester, 2-[2-(2-butoxyethoxy) ethoxy]ethyl thioester.

Thus the invention also provides a method of improving the biodegradability or reducing the toxicity of an imidazole cation containing ionic liquid comprising an ester, amide or thioester side chain at the 3-position of the imidazole ring by introducing at least one ether group into the side chain.

In another embodiment, the present invention provides a means of improving the biodegradability of the compounds of the invention by the introduction of an OctOSO$_3^-$ counter anion into the molecule.

In a related embodiment, the toxicity of an IL may be reduced by introduction of an ester functional group side chain into the 3 position of the imidazolium ring, wherein the ester functional group side chain comprises from 1-4 ether linkages. Compounds with side chains comprising 2-4 ether linkages are particularly preferred.

Thus, the invention provides a compound having a biodegradability of at least 60% which can be selected from the group consisting of:
KG38 (3-methyl-1-(2-[2-propoxy]ethoxycarbonylmethyl) imidazolium octylsulfate),
KG42 (3-methyl-1-(2-[2-propoxyethoxy]ethoxycarbonylmethyl)imidazolium octylsulfate),
KG44 (2,3-dimethyl-1-(2-[2-butoxy]ethoxycarbonylmethyl) imidazolium octylsulfate),
KG35 (3-methyl-1-(pentoxycarbonylmethyl)imidazolium octylsulfate),
KG39 (3-methyl-1-(2-[2-butoxy]ethoxycarbonylmethyl) imidazolium octylsulfate) and
KG43 (3-methyl-1-(2-[2-butoxyethoxy]ethoxycarbonylmethyl)imidazolium octylsulfate).

A compound having a biodegradability of at least 50% can be selected from the group consisting of:
KG34 (3-methyl-1-(butoxycarbonylmethyl)imidazolium octylsulfate),
KG36 (3-methyl-1-(2-[2-methoxy]ethoxycarbonylmethyl) imidazolium octylsulfate),
KG37 (3-methyl-1-(2-[2-ethoxy]ethoxycarbonylmethyl) imidazolium octylsulfate),
KG40 (3-methyl-1-(2-[2-methoxyethoxy]ethoxycarbonylmethyl)imidazolium octylsulfate),
KG41 (3-methyl-1-(2-[2-ethoxyethoxy]ethoxycarbonylmethyl)imidazolium octylsulfate) and
KG45 (2,3-dimethyl-1-(2-[2-methoxyethoxy]ethoxycarbonylmethyl)imidazolium octylsulfate.

IL compounds which are non-toxic to *Pseudomonas aeruginosa, Staphylococcus aureus, Escherichia coli, Enterococcus* sp., *Klebsiella* sp., *Bacillus subtilis Salmonella* sp., can be selected from the group consisting of:
KG7 (3-methyl-1-(2-[2-methoxy]ethoxycarbonylmethyl) imidazolium bromide),
KG8 (3-methyl-1-(2-[2-ethoxy]ethoxycarbonylmethyl)imidazolium bromide),
KG9 (3-methyl-1-(2-[2-propoxy]ethoxycarbonylmethyl) imidazolium bromide),
KG10 (3-methyl-1-(2-[2-butoxy]ethoxycarbonylmethyl) imidazolium bromide),
KG12 (3-methyl-1-(2-[2-methoxyethoxy]ethoxycarbonylmethyl)imidazolium bromide),
KG13 (3-methyl-1-(2-[2-ethoxyethoxy]ethoxycarbonylmethyl)imidazolium bromide),
KG14 (3-methyl-1-(2-[2-propoxyethoxy]ethoxycarbonylmethyl)imidazolium bromide),
KG15 (3-methyl-1-(2-[2-butoxyethoxy]ethoxycarbonylmethyl)imidazolium bromide),
KG16 (2,3-dimethyl-1-(2-[2-butoxy]ethoxycarbonylmethyl) imidazolium bromide),
KG18 (2,3-dimethyl-1-(2-[2-methoxyethoxy]ethoxycarbonylmethyl)imidazolium bromide),
KG23 (3-methyl-1-(2-[2-methoxy]ethoxycarbonylmethyl) imidazolium PF$_6$),
KG24 (3-methyl-1-(2-[2-ethoxy]ethoxycarbonylmethyl) imidazolium PF$_6$),
KG25 (3-methyl-1-(2-[2-propoxy]ethoxycarbonylmethyl) imidazolium PF$_6$),
KG26 (3-methyl-1-(2-[2-butoxy]ethoxycarbonylmethyl) imidazolium PF$_6$),
KG27 (3-methyl-1-(2-[2-methoxyethoxy]ethoxycarbonylmethyl)imidazolium PF$_6$),
KG28 (3-methyl-1-(2-[2-ethoxyethoxy]ethoxycarbonylmethyl)imidazolium PF$_6$),
KG29 (3-methyl-1-(2-[2-propoxyethoxy]ethoxycarbonylmethyl)imidazolium PF$_6$),
KG30 (3-methyl-1-(2-[2-butoxyethoxy]ethoxycarbonylmethyl)imidazolium PF$_6$),
KG32 (2,3-dimethyl-1-(2-[2-butoxy]ethoxycarbonylmethyl) imidazolium PF$_6$),
KG33 (2,3-dimethyl-1-(2-[2-methoxyethoxy]ethoxycarbonylmethyl)imidazolium PF$_6$).
KG38 (3-methyl-1-(2-[2-propoxy]ethoxycarbonylmethyl) imidazolium octylsulfate),
KG42 (3-methyl-1-(2-[2-propoxyethoxy]ethoxycarbonylmethyl)imidazolium octylsulfate),
KG44 (2,3-dimethyl-1-(2-[2-butoxy]ethoxycarbonylmethyl) imidazolium octylsulfate),
KG35 (3-methyl-1-(pentoxycarbonylmethyl)imidazolium octylsulfate),
KG39 (3-methyl-1-(2-[2-butoxy]ethoxycarbonylmethyl) imidazolium octylsulfate),
KG43 (3-methyl-1-(2-[2-butoxyethoxy]ethoxycarbonylmethyl)imidazolium octylsulfate),
KG34 (3-methyl-1-(butoxycarbonylmethyl)imidazolium octylsulfate),
KG36 (3-methyl-1-(2-[2-methoxy]ethoxycarbonylmethyl) imidazolium octylsulfate), KG37 (3-methyl-1-(2-[2-ethoxy]ethoxycarbonylmethyl) imidazolium octylsulfate),
KG40 (3-methyl-1-(2-[2-methoxyethoxy]ethoxycarbonylmethyl)imidazolium octylsulfate),
KG41 (3-methyl-1-(2-[2-ethoxyethoxy]ethoxycarbonylmethyl)imidazolium octylsulfate),
KG45 (2,3-dimethyl-1-(2-[2-methoxyethoxy]ethoxycarbonylmethyl)imidazolium octylsulfate.
KG49 (3-methyl-1-(2-[2-methoxy]ethoxycarbonylmethyl) imidazolium $NTf_2$),
KG50 (3-methyl-1-(2-[2-ethoxy]ethoxycarbonylmethyl) imidazolium $NTf_2$),
KG51 (3-methyl-1-(2-[2-propoxy]ethoxycarbonylmethyl) imidazolium $NTf_2$),
KG52 (3-methyl-1-(2-[2-butoxy]ethoxycarbonylmethyl) imidazolium $NTf_2$),
KG53 (3-methyl-1-(2-[2-methoxyethoxy]ethoxycarbonylmethyl)imidazolium $NTf_2$),
KG54 (3-methyl-1-(2-[2-ethoxyethoxy]ethoxycarbonylmethyl)imidazolium $NTf_2$),
KG55 (3-methyl-1-(2-[2-propoxyethoxy]ethoxycarbonylmethyl)imidazolium $NTf_2$),
KG56 (3-methyl-1-(2-[2-butoxyethoxy]ethoxycarbonylmethyl)imidazolium $NTf_2$),
KG58 (2,3-dimethyl-1-(2-[2-butoxy]ethoxycarbonylmethyl) imidazolium $NTf_2$),
KG59 (2,3-dimethyl-1-(2-[2-methoxyethoxy]ethoxycarbonylmethyl)imidazolium $NTf_2$).
KG62 (3-methyl-1-(2-[2-methoxy]ethoxycarbonylmethyl) imidazolium $BF_4$),
KG63 (3-methyl-1-(2-[2-ethoxy]ethoxycarbonylmethyl) imidazolium $BF_4$),
KG64 (3-methyl-1-(2-[2-propoxy]ethoxycarbonylmethyl) imidazolium $BF_4$),
KG65 (3-methyl-1-(2-[2-butoxy]ethoxycarbonylmethyl) imidazolium $BF_4$),
KG66 (3-methyl-1-(2-[2-methoxyethoxy]ethoxycarbonylmethyl)imidazolium $BF_4$),
KG67 (3-methyl-1-(2-[2-ethoxyethoxy]ethoxycarbonylmethyl)imidazolium $BF_4$),
KG68 (3-methyl-1-(2-[2-propoxyethoxy]ethoxycarbonylmethyl)imidazolium $BF_4$),
KG69 (3-methyl-1-(2-[2-butoxyethoxy]ethoxycarbonylmethyl)imidazolium $BF_4$),
KG71 (2,3-dimethyl-1-(2-[2-butoxy]ethoxycarbonylmethyl) imidazolium $BF_4$),
KG72 (2,3-dimethyl-1-(2-[2-methoxyethoxy]ethoxycarbonylmethyl)imidazolium $BF_4$).
KG75 (3-methyl-1-(2-[2-methoxy]ethoxycarbonylmethyl) imidazolium $N(CN)_2$),
KG76 (3-methyl-1-(2-[2-ethoxy]ethoxycarbonylmethyl) imidazolium $N(CN)_2$),
KG77 (3-methyl-1-(2-[2-propoxy]ethoxycarbonylmethyl) imidazolium $N(CN)_2$),
KG78 (3-methyl-1-(2-[2-butoxy]ethoxycarbonylmethyl) imidazolium $N(CN)_2$),
KG79 (3-methyl-1-(2-[2-methoxyethoxy]ethoxycarbonylmethyl)imidazolium $N(CN)_2$),
KG80 (3-methyl-1-(2-[2-ethoxyethoxy]ethoxycarbonylmethyl)imidazolium $N(CN)_2$),
KG81 (3-methyl-1-(2-[2-propoxyethoxy]ethoxycarbonylmethyl)imidazolium $N(CN)_2$),
KG82 (3-methyl-1-(2-[2-butoxyethoxy]ethoxycarbonylmethyl)imidazolium $N(CN)_2$),
KG84 (2,3-dimethyl-1-(2-[2-butoxy]ethoxycarbonylmethyl) imidazolium $N(CN)_2$) and
KG85 (2,3-dimethyl-1-(2-[2-methoxyethoxy]ethoxycarbonylmethyl)imidazolium $N(CN)_2$).
KG422 (3-methyl-1-[1-methoxyethyl]carbamylmethyl)imidazolium bromide)
KG405 (3-methyl-1-[bis-1-methoxyethyl]carbamylmethyl) imidazolium octylsulfate) and
KG407 (3-methyl-1-[bis-1-methoxyethyl]carbamylmethyl) imidazolium bromide).

Advantageously, many of the compounds of the invention produce a score of over 60% biodegradability over 28 days in a biodegradability test such as the Sturm Test, the Closed Bottle Test (OECD 301D) or the $CO_2$ Headspace Test (ISO 14593).

In a related embodiment, the compounds described herein can be used as solvents for chemical reactions, biofuel preparation or biomass dissolution. Examples of biomass dissolution reactions in which the ILs of the invention can be used include, but are not limited to, the dissolution of cellulose (which has been demonstrated for related polyether ILs (19)). The ILs of the invention may be advantageously used in biomass dissolutions since the low microbial toxicity and biocompatibility of the ILs is favourable to allow further biocatalytic or enzymatic reactions on the dissolved cellulose. Using the ILs of the invention, dissolution of cellulose at a level of at least 0.6% by mass (e.g., KG81, 150° C., 30 minutes), even with the less favourable DCA (dicyanoamide) counter-anion have been achieved. Other groups have demonstrated cellulose dissolution for related polyether ILs (19)], but the ILs claimed have the added advantage that their low microbial toxicity and bio-compatibility are favourable properties for further biocatalytic or enzymatic reactions on the dissolved cellulose.

The compounds described herein can be also be used in chemical reactions as solvents or co-solvents. Examples include, but are not limited to, enzymatic and biocatalytic reactions, neutralizations, acidifications and basifications, oxidations, hydrogenation reaction, reduction reactions, radical reactions, electrophilic additions, electrophilic substitutions, nucleophilic additions, nucleophilic substitutions, rearrangements, pericyclic reactions and metathesis reactions (with hydrogenation). It will be appreciated that such metathesis reactions (with hydrogenation) reactions must be of the kind generally compatible with an ester or amide linkage, for example, reactions involving nucleophiles such as hydroxide, complex hydrides, Grignard or alkyllithiums reagents may not be compatible with an ester or amide groups.

The ILs of the invention have been found to be particularly useful in hydrogenation, pericyclic reactions and metathesis reactions, since the inclusion of ether oxygens in the IL side-chain, together with an appropriate counter anion confers special properties such as complexation to alkali metals and increased affinity for hydroxylic solvents. However, use of the compounds of the invention in chemical reactions including hydrogenation, pericyclic and metathesis reactions are particular preferred. Notable in this respect is the use of ILs KG48 or KG51 as solvents in the selective reduction of trans-cinnamaldehyde to hydrocinnamaldehyde in the presence of hydrogen gas and palladium supported on carbon as a catalyst.

In one particular example involving the use of the IL corresponding to KG51 in such chemical reactions has been found to be particularly favourable, since the presence of ether oxygens in the side-chain increase biodegradability and decrease toxicity. At the same time, the selectivity of the reduction is much higher than with conventional ILs such as 1-butyl-3-methylimidazolium octylsulfate (bmim OctOSO$_3$) (Table 11 and FIG. 10).

In a further example of the use of the ILs of the present invention in chemical reactions, the IL corresponding to KG51 has been found to be particularly useful as a solvent for the selective hydrogenation of the carbon-carbon double bond conjugated to the carbonyl group in benzyl cinnamate using hydrogen gas and palladium supported on carbon as a catalyst (FIG. 6). Such use avoids cleavage of the benzyl ester when hydrogen gas and palladium supported on carbon as a catalyst for the hydrogenation. The use of this IL is surprisingly superior to that of conventional ILs such as 1-butyl-3-methylimidazolium NTf$_2$ (bmimNTf$_2$) or 1-butyl-3-methylimidazolium octylsulfate (bmim OctOSO$_3$), since use of conventional ILs typically leads to hydrogenolysis of the benzyl ester, as well as hydrogenation of the carbon-carbon double bond conjugated to the carbonyl group (Table 13 and FIG. 11).

It will be appreciated that the compounds of the invention can incorporate any combination of the features described.

DETAILED DESCRIPTION OF INVENTION

The present invention provides excellent candidates for ionic liquids, which are stable and liquid at room temperature, are readily biodegradable and have low toxicities and containing coordinating side-chains.

The ILs produced herein can be tailored with regard to properties such as viscosity, melting point, hydrophobicity, toxicity and biodegradability, these being key parameters for solvent applications. Toxicity data and biodegradability data for the compounds of the present invention are set out below, as are examples of the use of some of the ionic liquids of the invention in chemical reactions, such as hydrogenation reactions where such use gives high percentage conversion and high product selectivity. Cellulose dissolution data is also presented.

Preparation of ILs

Figure 1:
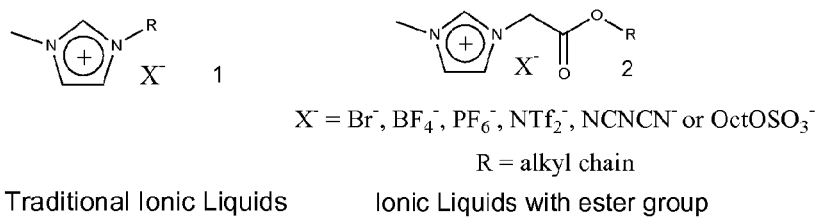
FIG. 1: Ionic Liquids.
Figure 2:
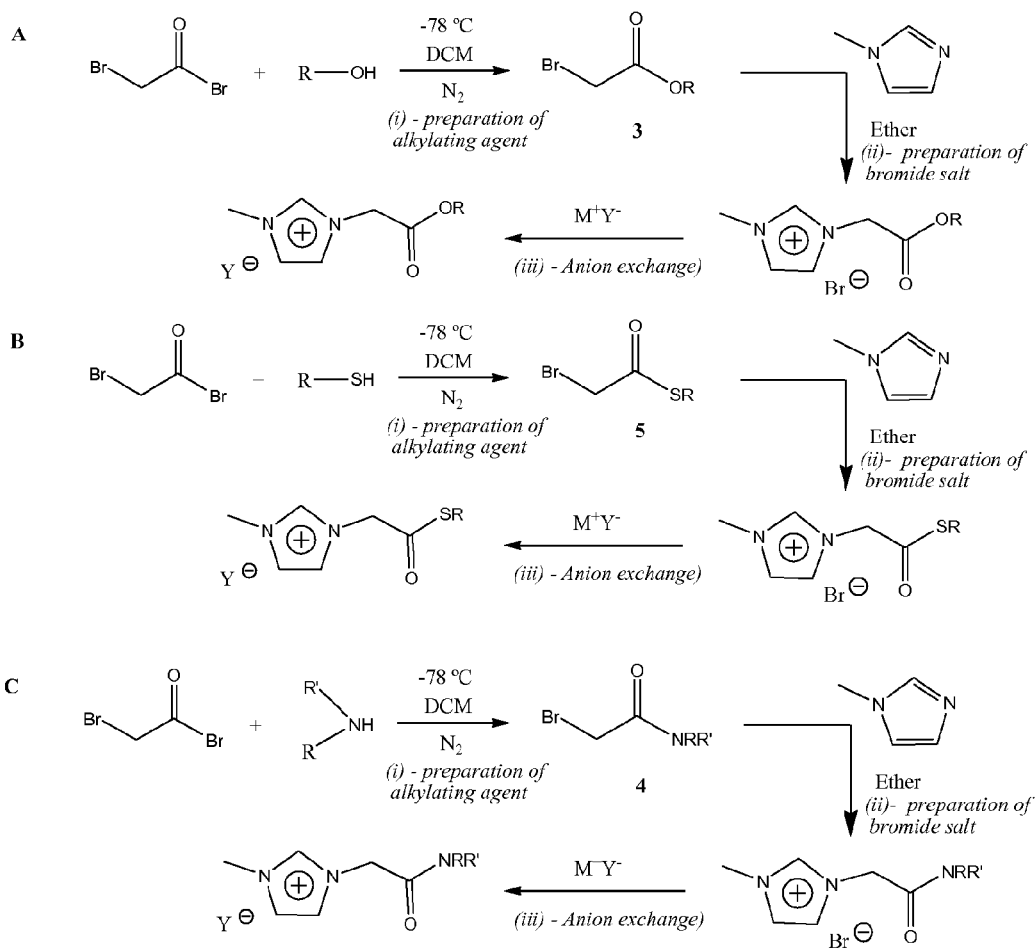
FIG. 2: Schemes A-C: Three Step Synthesis of Target Coordinating ILs.

A simple method to synthesize the family of ionic liquids has been developed which produced the ILs in good yield for each step. A typical reaction scheme for synthesis of the achiral ILs is shown in FIG. 2 (Scheme A-C). In brief, a bromo ester alkylating agent 3 is made from the alcohol of interest (ILs with thioester side chains or ILs with amide side chains can be typically prepared by use of a halo amide 4 or halo thioester 5 alkylating agent respectively). The bromo ester is then reacted with the imidazole of interest to form the bromide salt of the 2-imidazolium ester. A wide range of achiral alcohols were found to be compatible with the synthetic methodology outlined in FIG. 2, including unsaturated unsubstituted alkyl species such as 1-butanol and 1-pentanol, ether or polyether substituted species such as 2-ethoxyethanol and 2-(2-ethoxyethoxy)ethanol (Table 1). Use of the former produces ILs with unsubstituted alkyl ester side chains of desired length, whereas use of the latter provides unusual ILs possessing ether or polyether containing alkyl ester side chains. A large range of these types of ILs, possessing different properties have been made through the final synthetic anion exchange step from halide to different salts LiNTf$_2$, NaBF$_4$, KPF$_6$, NaN(CN)$_2$ and NaOctOSO$_3$. It will be appreciated that other related salts may be used to introduce the desired anions, for example, alkali metal salts comprising Na, K, Li and the appropriate anion may be used.

Step I: Preparation of Alkylating Agent

Typically, the first step (i) is the preparation of the alkylating agent obtained by reaction between the bromoacetyl bromide and different alcohols, amines or thiols. The reaction involving bromoacetyl bromide and alcohols was performed under a nitrogen atmosphere at −78° C. for 3 hours. After purification by distillation the corresponding bromoester in a yield ranging from 62-83% was obtained (Table 1). This reaction has been performed successfully on a broad range of scales from 10 mmol to 0.5 mol based on a 1 to 1.4 equivalence of bromoacetyl bromide with the different alcohols.

From 2-methoxyethyl to 2-(butoxyethoxy)-ethyl, all the bromoesters were purified by distillation. The higher molecular mass bromo ester derivatives were easily prepared in pure form on a large scale without the need for purification by column chromatography.

Step I: Alternative Preparation of Alkylating Agent

Typically, the first step (i) is the preparation of the alkylating agent obtained by reaction between the bromo acetyl bromide and different alcohols, amines or thiols. The reaction involving bromo acetyl bromide and alcohols was performed in the absence of solvent and promoted by neutral alumina. The reaction required typically 1 hour to reach completion, cooling with an ice bath during addition, then warming to RT without any requirement of an inert atmosphere, according to the procedure of Yadav (20). After purification by absorption of the crude reaction mixture onto excess solid NaHCO$_3$ and standing overnight, the solid was washed with toluene, filtered and the filtrate evaporated to give the corresponding bromoester in a yield typically around 88% (Table 1). This reaction has been performed successfully on a broad range of scales using at least 2 equivalents of bromo acetyl bromide with the different alcohols.

The bromides prepared by this method are pure enough to carry through to the subsequent imidazole alkylation without the need for purification by column chromatography.

Preparation of 2-(2-ethoxyethoxy)ethyl bromoacetate

To a stirred solution of DCM, diethylene glycol mono ethyl ether (21.0 mL, 150 mmol), and triethylamine (34.7 mL, 250 mmol) under a nitrogen atmosphere at −78° C. was added dropwise bromo acetyl bromide (17.2 mL, 200 mmol). After stirring at −78° C. for 3 h, the reaction mixture was allowed to warm up to −20° C. and quenched by addition of water (50 mL). The organic phase was washed with distilled water (3×50 mL), saturated ammonium chloride (3×50 mL), saturated sodium bicarbonate (3×50 mL) and brine (2×50 mL). The organic phase was then dried over magnesium sulfate, filtered and solvents removed via rotary evaporation to yield a crude product in 87% yield. This crude product was distilled (bp 105-115° C.) to give a colourless liquid at RT in 71% yield.

Alternative Preparation of 2-(2-ethoxyethoxy)ethyl bromoacetate

To diethylene glycol mono ethyl ether (21.0 mL, 150 mmol), and neutral alumina [e.g. Aldrich type WN-3] (17 g, 167 mmol) cooled with an ice-bath was added bromo acetyl bromide (44 mL, 500 mmol). The ice bath was removed and after 1 h standing at RT, the reaction mixture was poured onto solid NaHCO$_3$ in a glass filter funnel, with a cotton wool plug (effervescence). After standing overnight, the solid was washed with toluene until 200 ml of filtrate had been collected. The volatiles were removed via rotary evaporation to yield a crude product in 88% yield. This crude product was sufficiently pure to carry through to the next step. $^1$H δ ppm 4.34 (t, J=4.4 Hz, 2H), 3.88 (s, 2H), 3.74 (t, J=4.8 Hz, 2H), 3.66 (t, J=4.0 Hz, 2H), 3.60 (t, J=4.0 Hz, 2H), 3.53 (q, J=6.8 Hz, 2H), 1.22 (t, J=7.0 Hz, 3H)

Table 1 shows the alcohols converted to the bromo ester alkylating agents with isolated yields after distillation.

TABLE 1

Bromo esters containing ether and poly(ether) side-chains
(Reference compounds shown for comparative purposes)

| Alcohol | Bromo ester | Isolated Yield (%) |
|---|---|---|
|  1-Butanol Ref[11] | 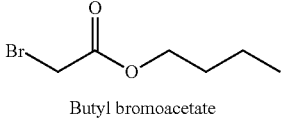 Butyl bromoacetate 11 | 88 |
| 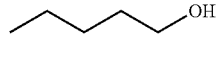 1-Pentanol Ref[11] | 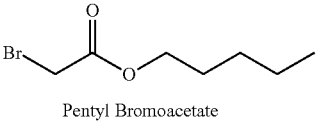 Pentyl Bromoacetate 11 | 64 |
| 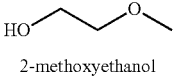 2-methoxyethanol | 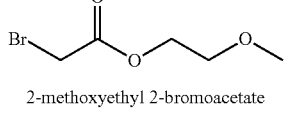 2-methoxyethyl 2-bromoacetate | 70 |
| 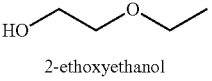 2-ethoxyethanol | 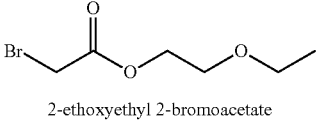 2-ethoxyethyl 2-bromoacetate | 81 |
| 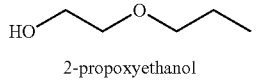 2-propoxyethanol | 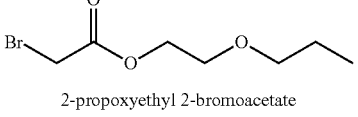 2-propoxyethyl 2-bromoacetate | 83 |
| 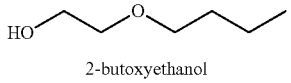 2-butoxyethanol | 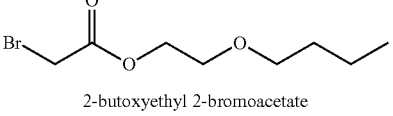 2-butoxyethyl 2-bromoacetate | 75 |
| 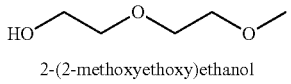 2-(2-methoxyethoxy)ethanol | 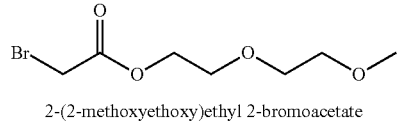 2-(2-methoxyethoxy)ethyl 2-bromoacetate | 78 |

TABLE 1-continued

Bromo esters containing ether and poly(ether) side-chains
(Reference compounds shown for comparative purposes)

| Alcohol | Bromo ester | Isolated Yield (%) |
|---|---|---|
| 2-(2-ethoxyethoxy)ethanol | 2-(2-ethoxyethoxy)ethyl 2-bromoacetate | 71 |
| 2-(2-propoxyethoxy)ethanol | 2-(2-propoxyethoxy)ethyl 2-bromoacetate | 73 |
| 2-(2-butoxyethoxy)ethanol | 2-(2-butoxyethoxy)ethyl 2-bromoacetate | 72 |
| 2-(2-(2-methoxyethoxy)ethoxy)ethanol | 2-(2-(2-methoxyethoxy)ethoxy)ethyl 2-bromoacetate | 62 |

Step II: Preparation of Bromide Salt

The second step (ii) is the preparation of the bromide salt. This reaction takes place between the 1-methylimidazole and the previously prepared family of bromo esters (Table 1) under a nitrogen atmosphere in diethyl ether solution at −15° C. for 3 hours then 18 hours at room temperature. The product precipitates and after washing and evaporation of the resulting solvent, the family of bromide salts was obtained in very good yield, between 82-98% (Table 2).

Most of the bromide salts are solids at room temperature, but with a low melting point (mp<100° C., current limit for definition as ionic liquids) with some examples melting close to room temperature (Table 2). Hence all the ester, ether ester or polyether ester imidazolium bromide salts prepared can be classified as ionic liquids.

Step III: Anion Exchange

The final synthetic step (iii) is an anion exchange. This exchange is important as it results in changes to the bulk solvent proprieties of the corresponding ionic liquid. The following salts were used salts $LiNTf_2$, $NaBF_4$, $KPF_6$, $NaN(CN)_2$, $NaOctOSO_3$. In most cases, anion exchange results in a melting point decrease compared to the bromide salt analogue, especially when $NTf_2^-$ is used as counter anion. $NTf_2^-$ and $N(CN)_2^-$ derivatives also have low viscosities, low viscosity being a key parameter for solvent applications. Hydrophobic ionic liquids can be made by using $NTf_2^-$ or $PF_6^-$ counter anions. Increasing biodegradability is achieved by using $OctOSO_3^-$ as the counter anion.

Anion Exchange Reactions Conditions $NTf_2$ ILs:

The reaction between $LiNTf_2$ and the bromide salt was realized in water at room temperature for 4 to 18 hours. After that time the corresponding hydrophobic Ionic liquids precipitated. After different washing the product was obtained with good yield (Table 2, column 3). All the resulting liquids are liquid at room temperature.

Preparation of
3-Methyl-1-(ethoxyethoxycarbonylmethyl)imidazolium $NTf_2^-$

A flask was charged with 3-Methyl-1-(ethoxyethoxycarbonylmethyl)imidazolium bromide (2.98 g, 10.0 mmol) and distilled water (10 mL). $LiNTf_2$ (4.59 g, 16.0 mmol) in distilled water (3 mL) was added in one portion and the suspension was stirred vigorously for 4 h at RT. The top aqueous layer was removed and the IL was washed with distilled water (3×10 mL). The solvent was then removed on the rotary evaporator and under high vacuum for 8 h to give a liquid at RT in 90% yield (4.42 g, 8.97 mmol). $^1H$ δ ppm 8.82 (s, 1H), 7.39 (t, J=1.8 Hz, 1H), 7.34 (t, J=1.8 Hz, 1H), 5.06 (s, 2H), 4.38 (t, J=4.6 Hz, 2H), 3.97 (s, 3H), 3.68 (t, J=4.6 Hz, 2H), 3.56 (q, J=7.2 Hz, 2H), 1.22 (t, J=7.0 Hz, 3H) $^{13}C$ δ ppm 165.76, 137.63, 123.80, 123.25, 67.62, 66.67, 65.97, 49.92, 36.56, 15.01

$PF_6$ ILs:

The exchange with $KPF_6$ was first completed using the same method as the $NTf_2$ ILs, but the yield was poor, even with extended reaction times. Optimisation of the reaction conditions required refluxing in acetone for 4 days. The yield obtained was very good, up to 90% in most cases (Table 2 column 5). Only two of those ionic liquids were solid but with a melting point less than 100° C.

Preparation of 3-Methyl-1-(methoxyethoxyethoxy-carbonylmethyl)imidazolium $PF_6^-$ A flask was charged with 3-Methyl-1-(methoxyethoxyethoxycarbonylmethyl)imidazolium bromide (3.51 g, 11.0 mmol) and acetone (10 mL). KPF$_6$ (3.31 g, 18.0 mmol) in acetone (5 mL) was added in one portion and the suspension was stirred vigorously for 4 days under reflux. The fine white precipitate was then filtered and washed with acetone (2×5 mL). The solvent was removed from the product on the rotary evaporator. The product was then dried under high vacuum for 4 h to give a viscous liquid at RT in 91% yield (3.87 g, 9.97 mmol). $^1$H δ ppm 8.60 (s, 1H), 7.52-7.50 (m, 2H), 5.13 (s, 2H), 4.44 (t, J=4.6 Hz, 2H), 4.00 (s, 3H), 3.81 (t, J=4.6 Hz, 2H), 3.71-3.67 (m, 2H), 3.61 (s, 2H) $^{13}$C δ ppm 165.98, 136.76, 123.33, 123.17, 71.16, 69.69, 67.85, 65.23, 57.54, 49.44, 35.84

BF$_4$ ILs:

The anion exchange was realized with NaBF$_4$ using the same new conditions as those used for the synthesis of the ionic liquid with PF$_6$ as anion. All the yields were excellent and up to 92% yield was obtained.

Preparation of 3-Methyl-1-(propoxyethoxyethoxycarbonylmethyl)imidazolium BF$_4^-$ A dry flask was charged with 3-Methyl-1-(propoxyethoxyethoxycarbonylmethyl)imidazolium bromide (2.94 g, 8.38 mmol) and acetone (10 mL) under a nitrogen atmosphere. NaBF$_4$ (1.11 g, 10.1 mmol) was added in one portion and the suspension was stirred vigorously for 4 days under reflux. The fine white precipitate was filtered quickly in air and washed with dry acetone (2×3 mL). The filtrate and washings were combined, solvent removed by rotary evaporation and then under high vacuum to give a slight viscous oil at RT in 93% yield (2.88 g, 8.21 mmol). $^1$H δ ppm 8.95 (s, 1H), 7.45 (t, J=1.8 Hz, 1H), 7.37 (t, J=1.8 Hz, 1H), 5.12 (s, 2H), 4.38 (t, J=4.6 Hz, 2H), 3.97 (s, 3H), 3.75 (t, J=4.8 Hz, 2H), 3.67 (t, J=3.2 Hz, 2H), 3.60 (t, J=3.2 Hz, 2H), 3.44 (t, J=10.8 Hz, 2H), 1.59-1.55 (m, 2H), 0.92 (t, J=7.6 Hz, 3H) $^{13}$C δ ppm 166.23, 137.96, 123.79, 123.13, 73.06, 70.54, 69.89, 68.54, 65.66, 49.85, 36.52, 22.75, 10.49

N(CN)$_2$ ILs:

For the exchange with NaN(CN)$_2$, different conditions were used. The acetone was substituted by acetonitrile and reflux was found not to be necessary. After 4 days the solution was filtered and washed to remove the precipitated NaBr salt. Good yields were obtained with the majority of the bromide salts used.

Preparation of 3-Methyl-1-(butoxycarbonylmethyl)imidazolium N(CN)$_2^-$

A dry flask was charged with 3-Methyl-1-(butoxycarbonylmethyl) imidazolium bromide (2.52 g, 11.00 mmol) and acetonitrile (10 mL) under a nitrogen atmosphere. NaN(CN)$_2$ (1.42 g, 16.00 mmol) was added in one portion and the suspension was stirred vigorously for 4 days at RT. The fine white precipitate was filtered quickly in air and washed with dry acetonitrile (2×1 mL). The filtrate and washings were combined, solvent removed by rotary evaporation and then under high vacuum to give a yellow oil at RT in 87% yield (2.50 g, 9.51 mmol). $^1$H δ ppm 9.82 (s, 1H), 7.56 (t, J=1.8 Hz, 1H), 7.46 (t, J=1.8 Hz, 1H), 5.32 (s, 2H), 4.15 (t, J=6.8 Hz, 2H), 4.02 (s, 3H), 1.61-1.58 (m, 2H), 1.33-1.27 (m, 2H), 0.87 (t, J=7.4 Hz, 3H) $^{13}$C δ ppm 164.10, 136.12, 121.89, 121.18, 64.85, 48.22, 34.87, 28.31, 16.96, 11.67

OctOSO$_3$ ILs:

With Na OctOSO$_3$, the reaction conditions were extensively optimised. According to the literature, the bromide salt and Na OctOSO$_3$ were stirred in water for 2 h at 60° C. The water was then slowly removed under vacuum. The precipitate was dissolved in DCM and washed with a small amount of distilled water. After evaporation of the solvent, the product was obtained in good yields up to 82%. However, the yield can decrease rapidly if caution is not taken during the washing. This is explained by the fact that the ionic liquid is extremely soluble in water and it is easy to lose compound during work-up. It is noted that 3 out of 13 of these OctOSO$_3$ ionic liquids are solid at room temperature although their melting points are still lower than 100° C.

Preparation of 3-Methyl-1-(propoxyethoxycarbonylmethyl)imidazolium octyl sulfate To a solution of 3-Methyl-1-(propoxyethoxycarbonylmethyl)imidazolium bromide (3.32 g, 12.0 mmol) in distilled water (20 mL) was added in one portion sodium octyl sulfate (2.09 g, 9.00 mmol) and stirred at 60° C. for 2 h. The water was then slowly removed under vacuum. The precipitate was dissolved in DCM (10 mL) and washed with distilled water (2×5 mL). The product remaining was dried on the rotary evaporator and then under high vacuum for 8 h to yield a dark yellow grease at RT in 85% yield (3.33 g, 7.64 mmol). $^1$H δ ppm 9.45 (s, 1H), 7.48 (t, J=1.6 Hz, 1H), 7.41 (t, J=1.6 Hz, 1H), 5.25 (5, 2H), 4.36 (t, J=4.8 Hz, 2H), 4.01 (s, 3H), 3.67 (t, J=4.6 Hz, 2H), 3.43 (t, J=6.8 Hz, 2H), 1.63-1.58 (m, 2H), 0.92-0.86 (m, 3H) $^{13}$C δ ppm 166.45, 138.89, 123.71, 123.06, 73.04, 67, 92, 67.89, 65.67, 49.91, 36.58, 31.83, 29.50, 29.36, 29.26, 25.87, 22.73, 22.66, 14.13, 10.47

TABLE 2

Library of 66 Coordinating ILs. All ILs are liquid at RT, unless mp range given in bold
(Reference compounds shown for comparative purposes)

| Ionic Liquid | Br$^-$ yield mp Range °C. | NTf$_2^-$ yield mp Range °C. | BF$_4^-$ yield mp Range °C. | PF$_6^-$ yield mp Range °C. | N(CN)$_2^-$ yield mp Range °C. | OctOSO$_3^-$ yield mp Range °C. |
|---|---|---|---|---|---|---|
| 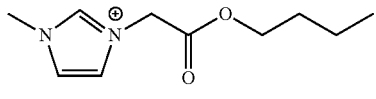 Ref$^{11}$ | 82 | 86 | 97 | 93 | 87 | 61 |
| 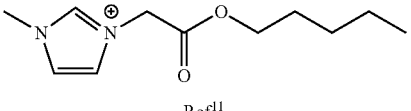 Ref$^{11}$ | 86 | 93 | 95 | 98 | 98 | 96 33-35 |

TABLE 2-continued

Library of 66 Coordinating ILs. All ILs are liquid at RT, unless mp range given in bold
(Reference compounds shown for comparative purposes)

| Ionic Liquid | Br⁻ yield mp Range °C. | NTf₂⁻ yield mp Range °C. | BF₄⁻ yield mp Range °C. | PF₆⁻ yield mp Range °C. | N(CN)₂⁻ yield mp Range °C. | OctOSO₃⁻ yield mp Range °C. |
|---|---|---|---|---|---|---|
| 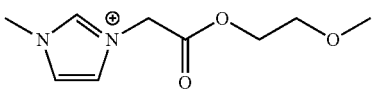 | 89 53-55 KG7 | 91 KG49 | 95 KG62 | 96 58-60 KG23 | 80 KG75 | 95 KG36 |
| 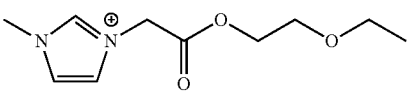 | 89 22-26 KG8 | 90 KG50 | 96 KG63 | 98 KG24 | 99 KG76 | 96 KG37 |
| 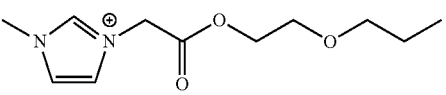 [SMILES: CCCOCCOC(=O)C[n+]1ccn(C)c1] | 88 25-30 KG9 | 69 KG51 | 97 KG64 | 97 KG25 | 91 KG77 | 85 KG38 |
| 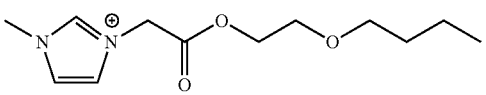 [SMILES: CCCCOCCOC(=O)C[n+]1ccn(C)c1] | 90 25-30 KG10 | 91 KG52 | 96 KG65 | 95 KG26 | 51 KG78 | 93 KG39 |
| 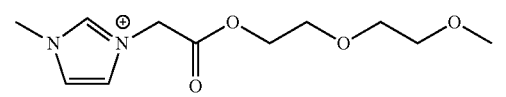 | 97 52-56 KG12 | 90 KG53 | 94 KG66 | 91 KG27 | 94 KG79 | 82 KG40 |
| 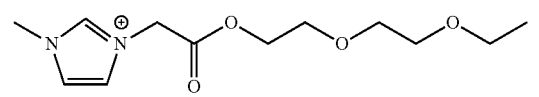 [SMILES: CCOCCOCCOC(=O)C[n+]1ccn(C)c1] | 92 28-32 KG13 | 87 KG54 | 96 KG67 | 96 KG28 | 93 KG80 | 93 KG41 |
| 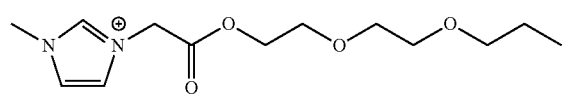 [SMILES: CCCOCCOCCOC(=O)C[n+]1ccn(C)c1] | 98 32-35 KG14 | 82 KG55 | 93 KG68 | 91 KG29 | 85 KG81 | 98 KG42 |
| 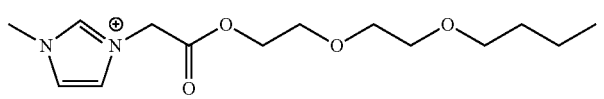 [SMILES: CCCCOCCOCCOC(=O)C[n+]1ccn(C)c1] | 94 48-52 KG15 | 86 KG56 | 92 KG69 | 80 KG30 | 98 KG82 | 92 KG43 |
| 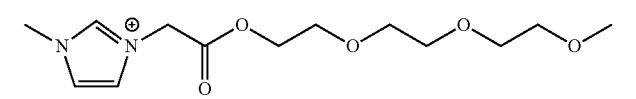 | 55 59-61 KG106 | 93 KG108 | 94 KG111 | 57 KG10 | 75 KG109 | 85 KG107 |
| 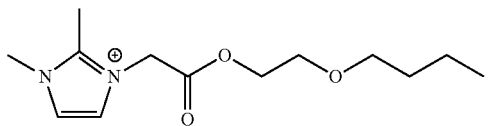 [SMILES: CCCCOCCOC(=O)C[n+]1ccn(C)c1C] | 92 KG16 | 83 KG58 | 95 KG71 | 97 KG32 | 78 KG84 | 84 50-54 KG45 |
| 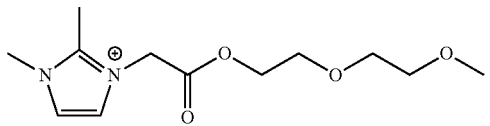 | 88 74-75 KG18 | 96 KG59 | 96 KG72 | 95 KG33 | 99 KG85 | 95 KG46 |

Preparation of Amide ILs

The method is analogous to the ester derivatives where the alcohol starting material is substituted for an amine.

Preparation of 2-bromo-N,N-bis(2-methoxyethyl)acetamide

To a stirred solution of DCM, bis(2-methoxyethyl)amine (40.0 g, 44.0 mL, 300 mmol), and triethylamine (69.25 mL, 500 mmol), under a nitrogen atmosphere at −78° C. was added drop wise bromo acetyl bromide (34.8 mL, 400 mmol). After stirring at −78° C. for 5 h, the reaction mixture was allowed to warm up to −20° C. and then quenched by addition of water (60 mL). The organic phase was washed with distilled water (3×30 mL), saturated ammonium chloride (3×30 mL), saturated sodium bicarbonate (3×30 mL) and brine (2×30 mL). The organic phase was then dried over magnesium sulfate, filtered and solvents removed via rotary evaporation to yield a crude product in 82% yield (62.3 g, 245 mmol). The crude product was then distilled under high vacuum at 170° C. to give pale yellow crystals in 49% yield (35.57 g, 140 mmol). Pure product can also be recrystallised from the crude material with diethyl ether.

$^1$H δ ppm 4.02 (s, 2H), 3.66 (t, J=5.2 Hz, 2H), 3.55 (br, 3H), 3.53 (t, J=5.0 Hz, 3H), 3.33 (s, 6H)

$^{13}$C δ ppm 167.79, 70.74, 70.27, 59.13, 58.94, 50.12, 46.90, 27.20

Preparation of (3-methyl-1-[bis-1-methoxyethyl]carbamylmethyl)imidazolium bromide To a stirred solution of 1-methylimidazole (45.0 mmol, 3.69 g, 3.58 mL, d: 1.030) in diethyl ether (100 mL) at −15° C. under a nitrogen atmosphere was added 2-bromo-N,N-bis(2-methoxyethyl)acetamide (50.0 mmol, 13.28 g) in diethyl ether. The reaction mixture was stirred vigorously at −15° C. for 2 h, then at RT overnight. The ether top phase was decanted and the product washed with ether (3×10 mL), the solvent removed on the rotary evaporator and dried under high vacuum for 8 h to give a white powder at RT in 91% yield (13.7 g, 40.8 mmol).

$^1$H δ ppm 9.91 (s, 1H), 7.44 (t, J=1.8 Hz, 1H), 7.42 (t, J=1.8 Hz, 1H), 5.66 (s, 2H), 4.07 (s, 3H), 3.70 (t, J=4.8 Hz, 2H), 3.57-3.55 (m, 4H), 3.50-0.47 (m, 2H), 3.36 (s, 3H), 3.31 (s, 3H) $^{13}$C δ ppm 165.46, 138.30, 124.14, 122.31, 70.51, 70.05, 59.25, 58.92, 50.63, 48.82, 46.83, 36.75

Preparation of (3-methyl-1-[bis-1-methoxyethyl]carbamylmethyl)imidazolium octylsulfate To a stirred solution of (3-methyl-1-[bis-1-methoxyethyl]carbamylmethyl)imidazolium bromide in distilled water (20 mL) was added in one portion sodium octyl sulfate (4.0 mmol, 0.93 g). The mixture was left stirring for 4 h, then the water was evaporated on the rotary evaporator. The remaining product was dissolved in DCM (10 mL) and washed with water (2×2 mL). The product was then dried on the rotary evaporator and under high vacuum for 8 h to give a viscous oil at RT in 92% yield (1.36 g, 2.75 mmol)

$^1$H δ ppm 9.34 (s, 1H), 7.25 (t, J=1.6 Hz, 1H), 7.20 (t, J=1.6 Hz, 1H), 5.30 (s, 2H) 3.91 (s, 3H), 3.60 (t, J=4.8 Hz, 2H), 3.51-3.43 (m, 6H), 3.30 (s, 3H), 3.26 (s, 3H)

$^{13}$C δ ppm 165.64, 139.03, 124.03, 122.17, 70.54, 70.03, 67.91, 59.17, 58.91, 50.43, 48.62, 46.77, 36.47, 31.83, 29.51, 29.36, 29.27, 25.87, 22.67, 14.13

Physical Properties of ILs Prepared and Their Suitability as Biodegradable Solvents Table 2 shows that all the solvents prepared can be characterized as ILs as their melting points are below 100° C. Closer examination of the table leads to the observation that nearly all are liquid at room temperature. This is an important property for these materials. The breadth of IL type, from short chain to long chain substituted imidazolium compounds, suggests great scope for the usefulness of the IL compounds.

Biodegradability Testing
Closed Bottle Test

The biodegradability of the test compounds was evaluated using the "Closed Bottle" test (OECD 301 D). (12) In this method, the chemical being evaluated is added to an aerobic aqueous medium inoculated with wastewater microorganisms and the depletion of dissolved molecular oxygen is measured for a defined period of time and reported as a percentage of the theoretical maximum. Compounds which reach a biodegradation level higher than 60% are referred to as "readily biodegradable". Sodium n-dodecyl sulfate (SDS) was used as reference substance. Solutions containing 2 mg L$^{-1}$ of the test ionic liquids and the reference chemical as sole sources of organic carbon were prepared, separately, in previously aerated mineral medium. The solutions were then inoculated with secondary effluent collected from an activated sludge treatment plant and each well-mixed solution was carefully dispensed into a series of biochemical oxygen demand (BOD) bottles so that all the bottles were completely full. A control with inoculum, but without test chemicals was run parallel for the determination of oxygen blanks. Duplicate bottles of each series were analysed immediately for dissolved oxygen and the remaining bottles were incubated at 20° C.±1° C. in the dark. Bottles of all series were withdrawn in duplicate for dissolved oxygen analysis over the 28 day incubation period. The biodegradation after n days was expressed as the ratio of the BOD to the chemical oxygen demand (COD) both of them expressed as mg O$_2$ per mg compound. The chemical oxygen demand was determined by the dichromate reflux method. (13, 21) For the calculation of the biochemical oxygen demand the determined oxygen depletions were divided by the concentration of ionic liquid.

CO$_2$ Headspace Test

To evaluate the biodegradability of the test ionic liquids, the "CO$_2$ Headspace" test (ISO 14593) (14) was also applied. This method allows the evaluation of the ultimate aerobic biodegradability of an organic compound in aqueous medium at a given concentration of microorganisms by analysis of inorganic carbon. The test ionic liquid, as the sole source of carbon and energy, was added at a concentration of 40 mg L$^{-1}$ to a mineral salt medium. These solutions were inoculated with activated sludge collected from an activated sludge treatment plant, washed and aerated prior to use and incubated in sealed vessels with a headspace of air. Biodegradation (mineralization to carbon dioxide) was determined by measuring the net increase in total organic carbon (TOC) levels over time.

Biodegradability Testing Results

The octylsulfate anion based achiral ILs gave the best biodegradation test results. ILs:

KG34: (3-methyl-1-(butoxycarbonylmethyl)imidazolium octylsulfate);

KG36: (3-methyl-1-(methoxyethoxycarbonylmethyl)imidazolium octylsulfate);

KG38: (3-methyl-1-(propoxyethoxycarbonylmethyl)imidazolium octylsulfate);

KG40: (3-methyl-1-(methoxyethoxyethoxycarbonylmethyl) imidazolium octylsulfate);

KG42: (3-methyl-1-(propoxyethoxyethoxycarbonylmethyl) imidazolium octylsulfate)

KG44: (2,3-dimethyl-1-(butoxyethoxycarbonylmethyl)imidazolium octylsulfate

KG35: (3-methyl-1-(pentoxycarbonylmethyl)imidazolium octylsulfate);

KG37: (3-methyl-1-(ethoxyethoxycarbonylmethyl)imidazolium octylsulfate);

KG39: (3-methyl-1-(butoxyethoxycarbonylmethyl)imidazolium octylsulfate);

KG41: (3-methyl-1-(ethoxyethoxyethoxycarbonylmethyl) imidazolium octylsulfate).

KG43: (3-methyl-1-(butoxyethoxyethoxycarbonylmethyl) imidazolium octylsulfate) and KG45: (2,3-dimethyl-1-(methoxyethoxyethoxycarbonylmethyl)imidazolium octylsulfate.

KG35, 38, 39, 42, 43, 44 passed the CO$_2$-Headspace test (at least 60% over 28 days duration) and clearly are "readily biodegradable" according to this test (see Tables 3 and 4). KG34, 36, 37, 40, 41, 45 all show significant biodegradation properties (between 55-59% in CO$_2$-Headspace test) and a significant improvement on the negligible biodegradation result obtained for bmimBF$_4$ and bmimPF$_6$. (9)

TABLE 3

| | CO$_2$-Headspace Test Results | | | | | |
|---|---|---|---|---|---|---|
| | | \multicolumn{5}{c}{Test time (days)} |
| | | 0 | 7 | 15 | 21 | 28 |
| | | \multicolumn{5}{c}{% Biodegradation} |
| SDS Ref | [structure] | 0 | 81 | 85 | 90 | 92 |
| KG34 | [structure] | 0 | 45 | 54 | 56 | 59 |
| KG36 | [structure] | 0 | 54 | 59 | 59 | 59 |
| KG38 | [structure] | 0 | 51 | 58 | 61 | 65 |
| KG40 | [structure] | 0 | 32 | 56 | 58 | 58 |
| KG42 | [structure] | 0 | 42 | 62 | 63 | 66 |
| KG44 | [structure] | 0 | 53 | 54 | 62 | 65 |

KG34: (3-methyl-1-(butoxycarbonylmethyl)imidazolium octylsulfate);

KG36: (3-methyl-1-(methoxyethoxycarbonylmethyl)imidazolium octylsulfate);

KG38: (3-methyl-1-(propoxyethoxycarbonylmethyl)imidazolium octylsulfate);

KG40: (3-methyl-1-(methoxyethoxyethoxycarbonylmethyl)imidazolium octylsulfate).

Figure 12:
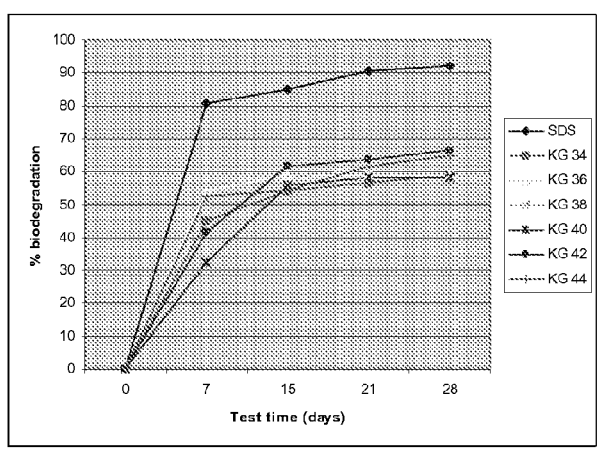
FIG. 12: Graph of $CO_2$ Headspace test results, corresponding to Table 3

KG42: (3-methyl-1-(propoxyethoxyethoxycarbonylmethyl)imidazolium octylsulfate) and KG44: (2,3-dimethyl-1-(butoxyethoxycarbonylmethyl)imidazolium octylsulfate See FIG. 12.

TABLE 4

CO$_2$-Headspace Test Results:

| | Test time (days) | | | | |
|---|---|---|---|---|---|
| | 0 | 7 | 15 | 21 | 28 |
| | % Biodegradation | | | | |
| SDS | 0 | 78 | 87 | 90 | 90 |
| KG35 | 0 | 52 | 59 | 60 | 64 |
| KG37 | 0 | 54 | 57 | 59 | 57 |
| KG39 | 0 | 53 | 59 | 60 | 61 |
| KG41 | 0 | 51 | 56 | 56 | 56 |
| KG43 | 0 | 56 | 61 | 64 | 65 |
| KG45 | 0 | 50 | 52 | 54 | 55 |

KG35: (3-methyl-1-(pentoxycarbonylmethyl)imidazolium octylsulfate);
KG37: (3-methyl-1-(ethoxyethoxycarbonylmethyl)imidazolium octylsulfate);
KG39: (3-methyl-1-(butoxyethoxycarbonylmethyl)imidazolium octylsulfate);
KG41: (3-methyl-1-(ethoxyethoxyethoxycarbonylmethyl)imidazolium octylsulfate).
KG43: (3-methyl-1-(butoxyethoxyethoxycarbonylmethyl)imidazolium octylsulfate) and
KG45: (2,3-dimethyl-1-(methoxyethoxyethoxycarbonylmethyl)imidazolium octylsulfate)

Figure 13:
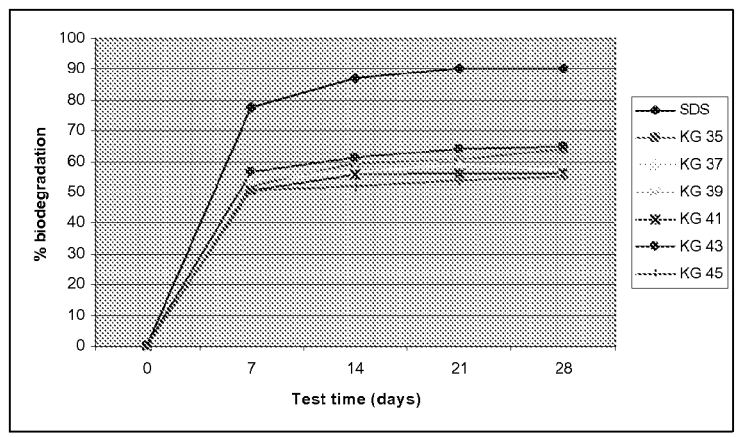
FIG. 13: Graph of $CO_2$ Headspace test results, corresponding to Table 4

See FIG. 13.

TABLE 5

CO$_2$-Headspace Test Results

| | | Test time (days) |
|---|---|---|
| | | 0    7    15    21    28 |
| | | % Biodegradation |
| SDS | Na$^+$ [dodecyl sulfate structure] | 0    74    81    86    85 |
| KG403 | [3-methyl-1-(pyrrolidinylcarbonylmethyl)imidazolium structure] OctOSO$_3^-$ Reference amide compound | 0    27    32    36    36 |
| KG404 | [2,3-dimethyl-1-(pyrrolidinylcarbonylmethyl)imidazolium structure] OctOSO$_3^-$ Reference amide compound | 0    26    30    35    35 |
| KG405 | [3-methyl-1-(N,N-dimethoxyethyl-carbamylmethyl)imidazolium structure] OctOSO$_3^-$ | 0    26    30    29    29 |

KG403: 3-methyl-1-(pyrrolidinylcarbonylmethyl)imidazolium octylsulfate
KG404: 2,3-dimethyl-1-(pyrrolidinylcarbonylmethyl)imidazolium octylsulfate
KG405: 3-methyl-1-(N,N-dimethoxyethyl-carbamylmethyl)imidazolium octylsulfate.

Figure 14:
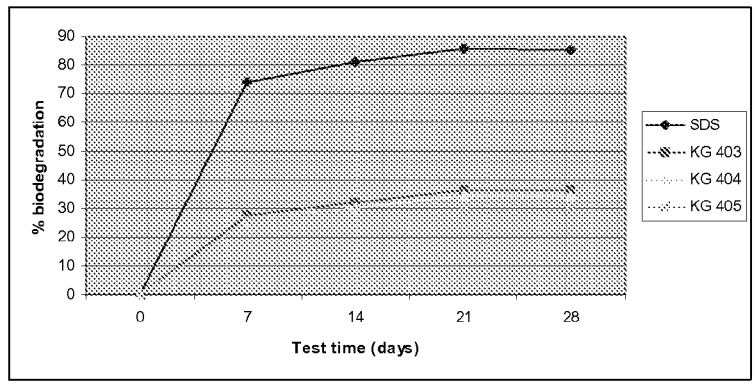
FIG. 14: Graph of $CO_2$ Headspace test results, corresponding to Table 5

See FIG. 14.

Toxicity of Prepared ILs

Seven strains of bacteria were used in the assessment of the antimicrobial activity of the ILs claimed: 4 gram negative and three gram positive as shown below.

| Gram negative bacteria | Gram positive bacteria |
|---|---|
| *Pseudomonas aeruginosa* | *Staphylococcus aureus* |
| *Escherichia coli* | *Enterococcus* sp. |
| *Klebsiella* sp. | *Bacillus subtilis* |
| *Salmonella* sp. | |

The minimum inhibitory concentrations were measured for those ILs which showed activity. A wide concentration range was tested (0-20000 μg/ml). The concentrations screened for antibacterial activity are generally from 2 μg/ml to 1000 μg/ml (Table 6). Potent antibacterial compounds will have MIC values at the lower end of this range, compounds which have MIC values at the higher end of the range, show antibacterial activity but at levels not significant for antibacterial drug development. The concentration range screened for the ILs containing ethers was up to 20000 μg/ml. At these high concentrations a lack of antibacterial activity is a significant result. IL examples containing a hydrocarbon side chain, or an ester with a long hydrocarbon chain have proven potent antibacterial properties (Table 7 and References 9, 12).

TABLE 6

Toxicity Results

| Structure | MIC values (μg/ml) | | | | | |
|---|---|---|---|---|---|---|
| | Br | $PF_6$ | $OctOSO_3$ | $NTf_2$ | $BF_4$ | $N(CN)_2$ |
| 1-methylimidazolium, butyl ester | >20000 KG19 | >20000 KG21 | 5000 KG34 | 10000 KG47 | >20000 KG60 | 5000 KG73 |
| 1-methylimidazolium, pentyl ester | >20000 KG17[11] | >20000 KG22 | >20000 KG35[11] | 10000 KG48 | 10000 KG61 | 10000 KG74 |
| 1-methylimidazolium, 2-methoxyethyl ester | >20000 KG7 | >20000 KG23 | >20000 KG36 | 10000 KG49 | >20000 KG62 | >20000 KG75 |
| 1-methylimidazolium, 2-ethoxyethyl ester | >20000 KG8 | >20000 KG24 | >20000 KG37 | >20000 KG50 | >20000 KG63 | >20000 KG76 |
| 1-methylimidazolium, 2-propoxyethyl ester | >20000 KG9 | >20000 KG25 | >20000 KG38 | 10000 KG51 | >20000 KG64 | >20000 KG77 |
| 1-methylimidazolium, 2-butoxyethyl ester | >20000 KG10 | >20000 KG26 | >20000 KG39 | >20000 KG52 | >20000 KG65 | >20000 KG78 |
| 1-methylimidazolium, methoxyethoxyethyl ester | >20000 KG12 | 2500 KG27 | >20000 KG40 | 10000 KG53 | >20000 KG66 | >20000 KG79 |
| 1-methylimidazolium, ethoxyethoxyethyl ester | >20000 KG13 | >20000 KG28 | 10000 KG411 | >20000 KG54 | >20000 KG67 | >20000 KG80 |
| 1-methylimidazolium, propoxyethoxyethyl ester | >20000 KG14 | >20000 KG29 | >20000 KG42 | >20000 KG55 | >20000 KG68 | >20000 KG81 |
| 1-methylimidazolium, butoxyethoxyethyl ester | >20000 KG15 | >20000 KG30 | 10000 KG43 | >20000 KG56 | >20000 KG69 | >20000 KG82 |
| 1,2-dimethylimidazolium, pentyl ester | >20000 KG11 | >20000 KG31 | >20000 KG44 | >20000 KG57 | 5000 KG70 | >20000 KG83 |
| 1,2-dimethylimidazolium, 2-butoxyethyl ester | >20000 KG16 | >20000 KG32 | 10000 KG45 | >20000 KG58 | >20000 KG71 | >20000 KG84 |
| 1,2-dimethylimidazolium, methoxyethoxyethyl ester | >20000 KG18 | >20000 KG33 | 10000 KG46 | >20000 KG59 | >20000 KG72 | >20000 KG85 |

TABLE 6-continued

Toxicity Results

| | MIC values (μg/ml) | | | | | |
|---|---|---|---|---|---|---|
| | Br | PF$_6$ | OctOSO$_3$ | NTf$_2$ | BF$_4$ | N(CN)$_2$ |
| 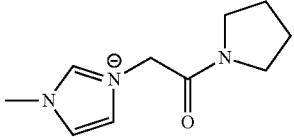<br>Reference amide compound | >20000<br>KG420 | | >20000<br>KG403 | | | |
| 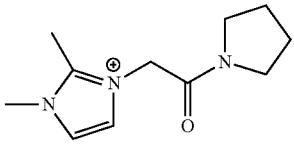<br>Reference amide compound | >20000<br>KG421 | | >20000<br>KG404 | | | |
| 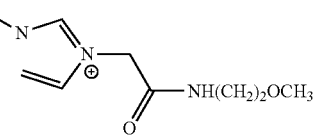 | >20000<br>KG422 | | | | | |
| 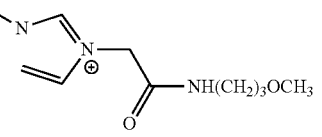 | >20000<br>KG423 | | | | | |
| 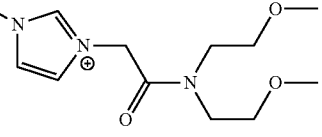 | >20000<br>KG407 | | >20000<br>KG405 | | | |

Toxicity Results

Figure 3:
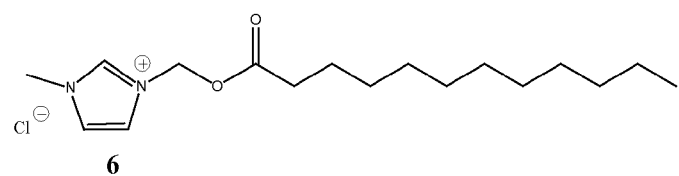
FIG. 3: Comparison of structure of (6) 1-[(n-Dodecanoyloxy)methyl]-3-methylimidazolium Chloride and KG20 (3-methyl-1-(decanoxycarbonylmethyl)imidazolium bromide. Both are potent antibacterials.
Figure 3:
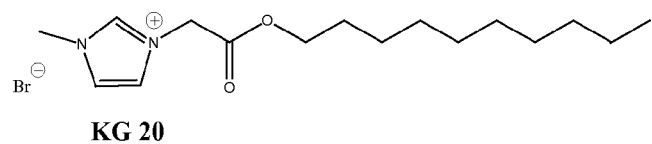

In general, the toxicities of the ionic liquids of the present invention are found to be some orders of magnitude lower than those of conventional solvents such as acetone and methanol. As previously mentioned, a common problem with the toxicity of ionic liquids is associated with the presence of an extended hydrocarbon chain. The length of the side chains was found to influence the dialkylimidazolium ionic liquids toxicity, with longer chain length provide to be more toxic. Bodor et al. (9) have showed that the long chain ester derivatives of methyl imidazole (shown as compound 6 in FIG. 3) show effective antimicrobial activity at ppm concentrations. Compound 6, FIG. 3 (9) appears similar to the family of ionic liquids of the present invention, except the fact that a different side of the chain is linked to the ester, and the inclusion of ether functional groups.

Figure 4:
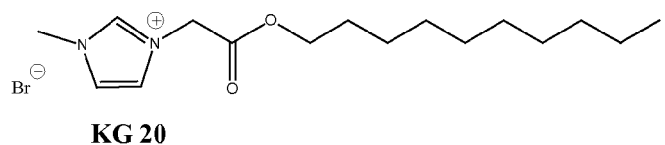
FIG. 4: Comparison of KG20 (3-methyl-1-(decanoxycarbonylmethyl)imidazolium bromide, a potent antibacterial and KG 15 (3-methyl-1-(2-[2-butoxyethoxy]ethoxycarbonylmethyl)imidazolium bromide), a low toxicity ionic liquid.
Figure 4:
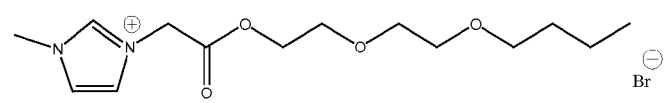
Figure 5:
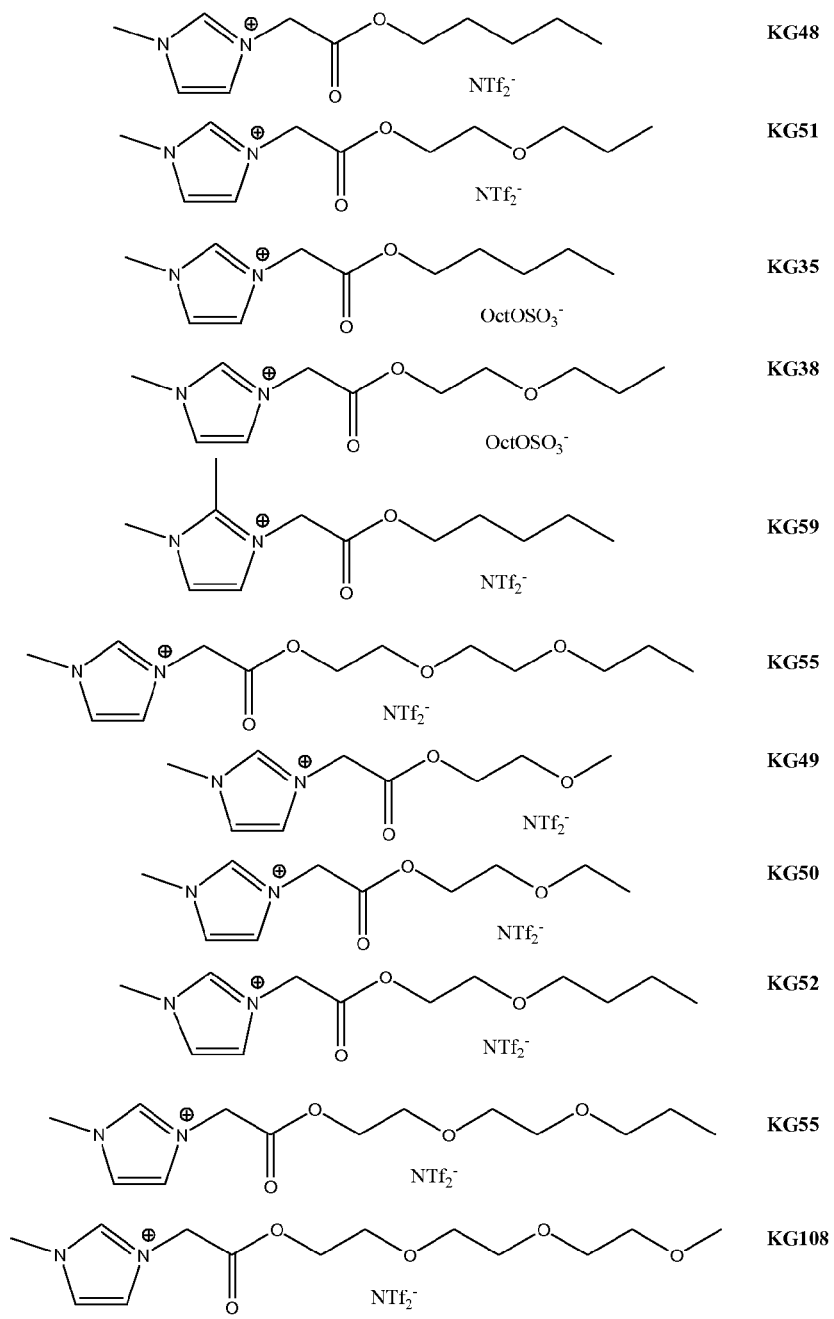
FIG. 5: Examples of Ionic liquids for use as reaction solvents.

Table 6 shows that all the ionic liquids prepared show significantly lower toxicity than derivatives without ester and ether or polyether functional groups (FIG. 4). KG 405, 422, 423 and 407 show that the presence of oxygen atoms in the side chain of amide derivatives leads also to low toxicity ILs, when compared to ILs with hydrocarbon sidechains of similar size. (eg KG407 vs potent antibacterial dodecyl substituted imidazolium salts). KG 403, 404, 420, 421 were used as reference compounds, containing a substituted amide group without extended linear alkyl chains. These results have significant implications for the usefulness of the ILs, as the toxicity is exceptional low for ILs.

Chemical Names of the IL Compounds

KG7 (3-methyl-1-(2-[2-methoxy]ethoxycarbonylmethyl) imidazolium bromide),

KG8 (3-methyl-1-(2-[2-ethoxy]ethoxycarbonylmethyl)imidazolium bromide),

KG9 (3-methyl-1-(2-[2-propoxy]ethoxycarbonylmethyl) imidazolium bromide),

KG10 (3-methyl-1-(2-[2-butoxy]ethoxycarbonylmethyl) imidazolium bromide),

KG12 (3-methyl-1-(2-[2-methoxyethoxy]ethoxycarbonylmethyl)imidazolium bromide),

KG13 (3-methyl-1-(2-[2-ethoxyethoxy]ethoxycarbonylmethyl)imidazolium bromide),

KG14 (3-methyl-1-(2-[2-propoxyethoxy]ethoxycarbonylmethyl)imidazolium bromide),

KG15 (3-methyl-1-(2-[2-butoxyethoxy]ethoxycarbonylmethyl)imidazolium bromide)

KG16 (2,3-dimethyl-1-(2-[2-butoxy]ethoxycarbonylmethyl) imidazolium bromide),

KG18 (2,3-dimethyl-1-(2-[2-methoxyethoxy]ethoxycarbonylmethyl)imidazolium bromide).

KG23 (3-methyl-1-(2-[2-methoxy]ethoxycarbonylmethyl) imidazolium PF$_6$),

KG24 (3-methyl-1-(2-[2-ethoxy]ethoxycarbonylmethyl) imidazolium PF$_6$),
KG25 (3-methyl-1-(2-[2-propoxy]ethoxycarbonylmethyl) imidazolium PF$_6$),
KG26 (3-methyl-1-(2-[2-butoxy]ethoxycarbonylmethyl) imidazolium PF$_6$),
KG27 (3-methyl-1-(2-[2-methoxyethoxy]ethoxycarbonylmethyl)imidazolium PF$_6$),
KG28 (3-methyl-1-(2-[2-ethoxyethoxy]ethoxycarbonylmethyl)imidazolium PF$_6$),
KG29 (3-methyl-1-(2-[2-propoxyethoxy]ethoxycarbonylmethyl)imidazolium PF$_6$),
KG30 (3-methyl-1-(2-[2-butoxyethoxy]ethoxycarbonylmethyl)imidazolium PF$_6$),
KG32 (2,3-dimethyl-1-(2-[2-butoxy]ethoxycarbonylmethyl) imidazolium PF$_6$),
KG33 (2,3-dimethyl-1-(2-[2-methoxyethoxy]ethoxycarbonylmethyl)imidazolium PF$_6$).
KG38 (3-methyl-1-(2-[2-propoxy]ethoxycarbonylmethyl) imidazolium octylsulfate),
KG42 (3-methyl-1-(2-[2-propoxyethoxy]ethoxycarbonylmethyl)imidazolium octylsulfate),
KG44 (2,3-dimethyl-1-(2-[2-butoxy]ethoxycarbonylmethyl) imidazolium octylsulfate),
KG35 (3-methyl-1-(pentoxycarbonylmethyl)imidazolium octylsulfate),
KG39 (3-methyl-1-(2-[2-butoxy]ethoxycarbonylmethyl) imidazolium octylsulfate),
KG43 (3-methyl-1-(2-[2-butoxyethoxy]ethoxycarbonylmethyl)imidazolium octylsulfate),
KG34 (3-methyl-1-(butoxycarbonylmethyl)imidazolium octylsulfate),
KG36 (3-methyl-1-(2-[2-methoxy]ethoxycarbonylmethyl) imidazolium octylsulfate),
KG37 (3-methyl-1-(2-[2-ethoxy]ethoxycarbonylmethyl) imidazolium octylsulfate),
KG40 (3-methyl-1-(2-[2-methoxyethoxy]ethoxycarbonylmethyl)imidazolium octylsulfate),
KG41 (3-methyl-1-(2-[2-ethoxyethoxy]ethoxycarbonylmethyl)imidazolium octylsulfate),
KG45 (2,3-dimethyl-1-(2-[2-methoxyethoxy]ethoxycarbonylmethyl)imidazolium octylsulfate.
KG49 (3-methyl-1-(2-[2-methoxy]ethoxycarbonylmethyl) imidazolium NTf$_2$),
KG50 (3-methyl-1-(2-[2-ethoxy]ethoxycarbonylmethyl) imidazolium NTf$_2$),
KG51 (3-methyl-1-(2-[2-propoxy]ethoxycarbonylmethyl) imidazolium NTf$_2$),
KG52 (3-methyl-1-(2-[2-butoxy]ethoxycarbonylmethyl) imidazolium NTf$_2$),
KG53 (3-methyl-1-(2-[2-methoxyethoxy]ethoxycarbonylmethyl)imidazolium NTf$_2$),
KG54 (3-methyl-1-(2-[2-ethoxyethoxy]ethoxycarbonylmethyl)imidazolium NTf$_2$),
KG55 (3-methyl-1-(2-[2-propoxyethoxy]ethoxycarbonylmethyl)imidazolium NTf$_2$),
KG56 (3-methyl-1-(2-[2-butoxyethoxy]ethoxycarbonylmethyl)imidazolium NTf$_2$),
KG58 (2,3-dimethyl-1-(2-[2-butoxy]ethoxycarbonylmethyl) imidazolium NTf$_2$),
KG59 (2,3-dimethyl-1-(2-[2-methoxyethoxy]ethoxycarbonylmethyl)imidazolium NTf$_2$).
KG62 (3-methyl-1-(2-[2-methoxy]ethoxycarbonylmethyl) imidazolium BF$_4$),
KG63 (3-methyl-1-(2-[2-ethoxy]ethoxycarbonylmethyl) imidazolium BF$_4$),
KG64 (3-methyl-1-(2-[2-propoxy]ethoxycarbonylmethyl) imidazolium BF$_4$),
KG65 (3-methyl-1-(2-[2-butoxy]ethoxycarbonylmethyl) imidazolium BF$_4$),
KG66 (3-methyl-1-(2-[2-methoxyethoxy]ethoxycarbonylmethyl)imidazolium BF$_4$),
KG67 (3-methyl-1-(2-[2-ethoxyethoxy]ethoxycarbonylmethyl)imidazolium BF$_4$),
KG68 (3-methyl-1-(2-[2-propoxyethoxy]ethoxycarbonylmethyl)imidazolium BF$_4$),
KG69 (3-methyl-1-(2-[2-butoxyethoxy]ethoxycarbonylmethyl)imidazolium BF$_4$),
KG71 (2,3-dimethyl-1-(2-[2-butoxy]ethoxycarbonylmethyl) imidazolium BF$_4$),
KG72 (2,3-dimethyl-1-(2-[2-methoxyethoxy]ethoxycarbonylmethyl)imidazolium BF$_4$).
KG75 (3-methyl-1-(2-[2-methoxy]ethoxycarbonylmethyl) imidazolium N(CN$_2$),
KG76 (3-methyl-1-(2-[2-ethoxy]ethoxycarbonylmethyl) imidazolium N(CN)$_2$),
KG77 (3-methyl-1-(2-[2-propoxy]ethoxycarbonylmethyl) imidazolium N(CN)$_2$),
KG78 (3-methyl-1-(2-[2-butoxy]ethoxycarbonylmethyl) imidazolium N(CN)$_2$),
KG79 (3-methyl-1-(2-[2-methoxyethoxy]ethoxycarbonylmethyl)imidazolium N(CN)$_2$),
KG80 (3-methyl-1-(2-[2-ethoxyethoxy]ethoxycarbonylmethyl)imidazolium N(CN)$_2$),
KG81 (3-methyl-1-(2-[2-propoxyethoxy]ethoxycarbonylmethyl)imidazolium N(CN)$_2$),
KG82 (3-methyl-1-(2-[2-butoxyethoxy]ethoxycarbonylmethyl)imidazolium N(CN)$_2$),
KG84 (2,3-dimethyl-1-(2-[2-butoxy]ethoxycarbonylmethyl) imidazolium N(CN)$_2$),
KG85 (2,3-dimethyl-1-(2-[2-methoxyethoxy]ethoxycarbonylmethyl)imidazolium N(CN)$_2$).
KG420 (3-methyl-1-(pyrrolidinylcarbonylmethyl)imidazolium bromide),
KG421 (2,3-dimethyl-1-(pyrrolidinylcarbonylmethyl)imidazolium bromide),
KG403 (3-methyl-1-(pyrrolidinylcarbonylmethyl)imidazolium octylsulfate,
KG404 (2,3-dimethyl-1-(pyrrolidinylcarbonylmethyl)imidazolium octylsulfate,
KG405 (3-methyl-1-[bis-1-methoxyethyl]carbamylmethyl) imidazolium octylsulfate),
KG407 (3-methyl-1-[bis-1-methoxyethyl]carbamylmethyl) imidazolium bromide),
KG422 (3-methyl-1-[1-methoxyethyl]carbamylmethyl)imidazolium bromide) and
KG423 (3-methyl-1-[1-methoxypropyl]carbamylmethyl) imidazolium bromide), A test reference study with 1-methyl-3-decyloxy-carbonyl methylimidazole bromide salt KG20, known to be toxic due to the long alkyl chain, has been completed to provide reference data. This experiment compares, for the same side chain length, the impact of the presence of the oxygen (e.g. KG15) on toxicity. As expected KG20 was toxic to all the different bacteria screened (see Table 7), and in some cases even at low concentrations (Table 7. *E. coli, Enterococcus* sp. and *S. aureus*). A comparison of the result of the Table 7 to those from Table 6, (KG15), indicates that the presence of the oxygen in the side chain is crucial to suppress the toxicity.

TABLE 7

Percentage kill for seven strains of bacteria at various concentrations of KG20.

| Strain | KG20 Concentration (μg/ml) | | | | | | | | |
|---|---|---|---|---|---|---|---|---|---|
| | 1000 | 500 | 250 | 125 | 62.5 | 31.25 | 15.62 | 7.8 | 3.9 |
| *E. coli* | 91 | 82 | 92 | 92 | 37 | 28 | 17 | 8.5 | 10 |
| *Enterococcus* sp. | 96.4 | 84 | 83.4 | 49.5 | 48.7 | 18.7 | 23 | 6 | 6.5 |
| *P. aeruginosa* | 100 | 82 | 82 | 55.5 | 0 | 6 | 0 | 0 | 0 |
| *Salmonella* sp. | 86 | 88 | 73.5 | 58 | 10 | 0 | 0 | 0 | 0 |
| *Klebsiella* sp. | 91.8 | 68.2 | 64 | 21 | 7 | 0 | 0 | 0 | 0 |
| *S. aureus* | — | 96 | 93.8 | 80.7 | 90.3 | 86.4 | 88.2 | 90 | 66 |
| *B. subtilis* | 100 | 83.2 | 81.5 | 80.2 | 0 | 0 | 0 | 0 | 0 |

The incorporation of the ether or polyether sidechain into the structure of the ionic liquid reduces the toxicity of the ionic liquid compared to alkyl derivatives. The viscosities of the ionic liquids claimed are observed to be significantly lower than the alkyl derivatives known. The combination of the ester in the side chain with ether or polyether sidechain leads to imidazolium ionic liquids with considerably greater propensity to biodegrade. When the octylsulfate counterion is present then the greatest degree of biodegradation is observed.

Cellulose Dissolution in Non-Toxic ILs

The following example demonstrates the utility of non-toxic ionic liquids in cellulose dissolution, especially in cases where further biological processes (e.g. enzymatic transformations) may be required to be performed on the dissolved cellulose and a biologically benign medium is preferred. IL KG81 (0.84 g) was heated to 150° C., in a small beaker, stirring with a small Teflon-coated magnetic bead and cellulose powder (Avicel®PH-101, Fluka), 5 mg, was added in one portion. After stirring for 30 minutes the cellulose was observed to have dissolved in the ionic liquid. Thus the dissolution of cellulose at a level of at least 0.6% by mass can occur using KG81 at a temperature of 150° C., for 30 minutes. The dissolution may occur even with a less favourable DCA (dicyanoamide) counter-anion. Other groups have demonstrated cellulose dissolution for related polyether ILs (19)], but the ILs of the invention have the added advantage over previously reported IL cellulose dissolution since their low microbial toxicity and bio-compatibility are favourable for facilitating further biocatalytic or enzymatic reactions on the dissolved cellulose.

Selective Hydrogenation of Trans-Cinnamaldehyde and Hydrogenolysis-Free Hydrogenation of Benzyl Cinnamate in Non-Toxic ILs The following example demonstrates the utility of ionic liquids in hydrogenation reactions, for example, in hydrogenation reactions involving α,β-unsaturated aldehydes and in particular an α,β-unsaturated carbonyl, such as trans-cinnamaldehyde, benzyl cinnamate or allyl cinnamate, where control of selectivity is required. Thus, the ionic liquids of the present invention may be used to selectively hydrogenate trans-cinnamaldehyde to hydrocinnamaldehyde using a commercially available palladium catalyst in a non-toxic solvent environment. The selective hydrogenation extends to benzyl cinnamate, where the ester is protected from hydrogenolysis under similar conditions.

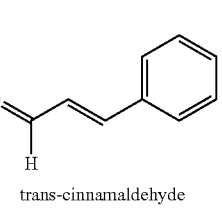

7 trans-cinnamaldehyde

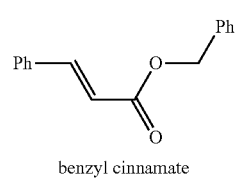

11 benzyl cinnamate

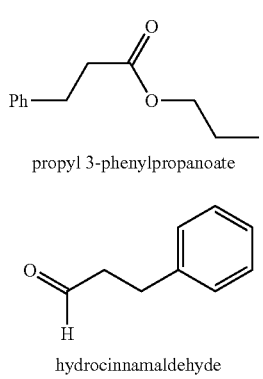

16 propyl 3-phenylpropanoate

8 hydrocinnamaldehyde

12 benzyl 3-phenylpropanoate

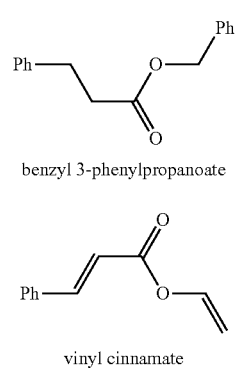

17 vinyl cinnamate

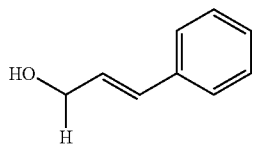

cinnamyl alcohol

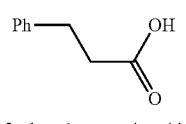

3-phenylpropanoic acid

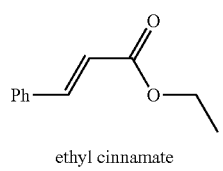

ethyl cinnamate

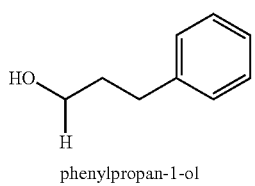

phenylpropan-1-ol

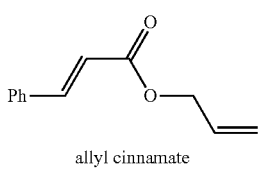

allyl cinnamate

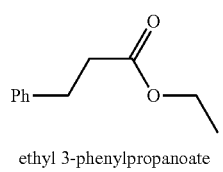

ethyl 3-phenylpropanoate

Hydrogenation Reaction Results

Trans-Cinnamaldehyde

Figure 6:
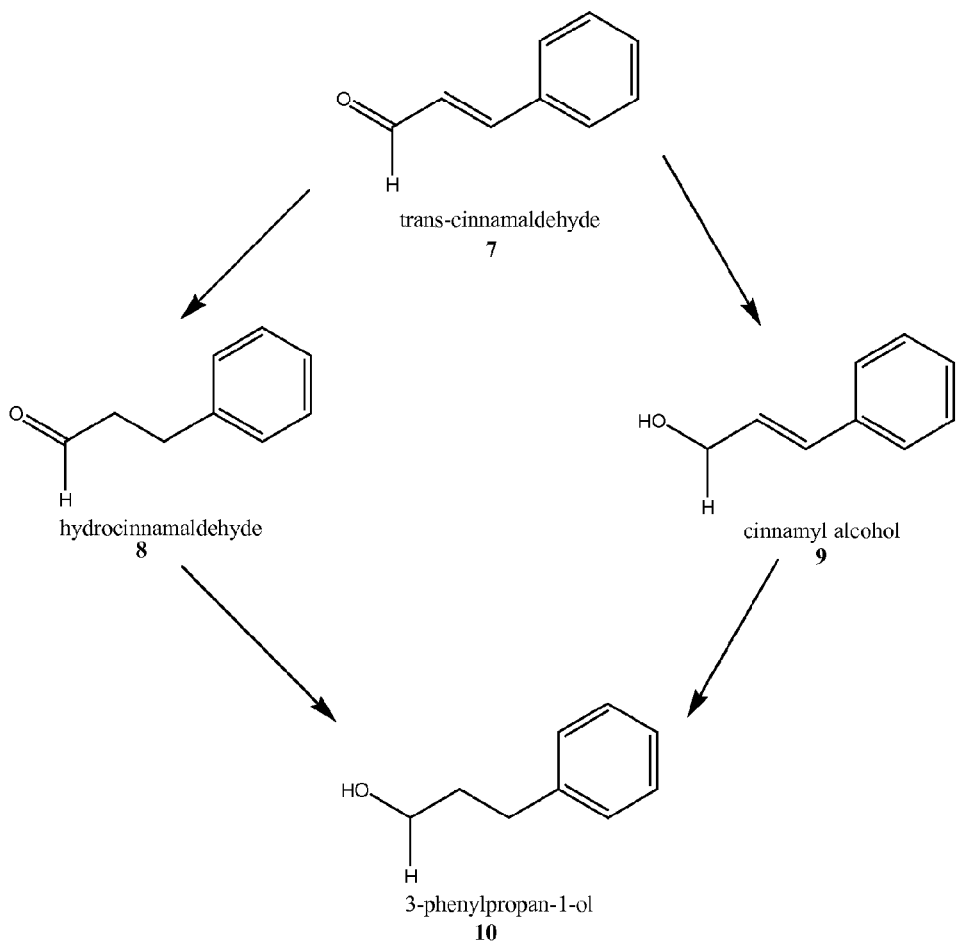
FIG. 6: Reduction pathways of trans-cinnamaldehyde.
Figure 7:
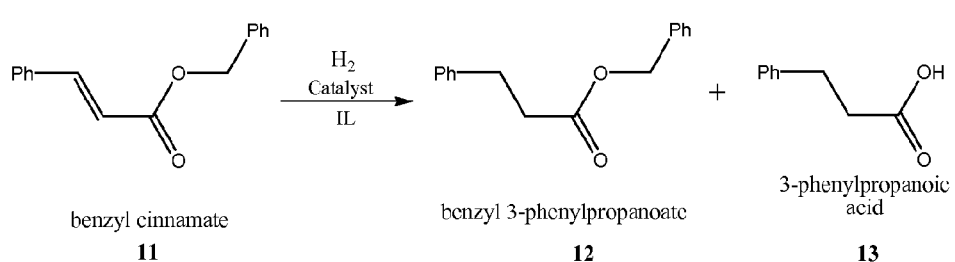
FIG. 7: Reduction of benzyl cinnamate.

Due to its highly conjugated system, the hydrogenation of the α,β-unsaturated aldehyde, trans cinnamaldehyde, usually leads to the reduction of the olefin moiety but also the carbonyl group, yielding the alcohol, 3-phenylpropanol (FIG. 6). The selective formation of hydrocinnamaldehyde is of both academic interest and of interest to the fine chemical industry (22).

Using the pentyl derivative (KG48) of the imidazolium ILs of the invention, selectivities generally ranged from 90 to 100%. The most impressive results obtained were achieved using the dimethyl derivative (KG59) of the ILs, where 100% conversion and selectivity were reached at 24 h upon the 1$^{st}$ recycle (Table 8). Although slight variations in conversion and selectivity occurred during the recycling procedure, almost the same reaction efficiency can be seen upon the fourth recycle (conversion 97%, selectivity 100%). (Table 8)

TABLE 8

Results from reactions using solvent (KG59) and (KG48)

| Solvent | Experiment (E)/ Recycle (R) | Time (h) | % Conversion | % Selectivity Product 8 |
|---|---|---|---|---|
| (KG59) | E1 | 24 | 8 | 100 |
|  |  | 48 | 36 | 100 |
|  | R1 | 24 | 100 | 100 |
|  |  | 48 | 100 | 93 |
|  | R2 | 24 | 48 | 73 |
|  |  | 48 | 97 | 98 |
|  | R3 | 24 | 79 | 99 |
|  |  | 48 | 100 | 96 |
|  | R4 | 24 | 89 | 100 |
|  |  | 48 | 97 | 100 |
| (KG48) | E1 | 48 | 98 | 94 |
|  | R1 | 48 | 100 | 93 |

When the IL side chain length is increased, or contains an oxygen atom, the result obtained does not vary significantly; the conversion remains consistent at 100% and the selectivity still does not decrease below 90%. Thus, the method is shown to be still applicable when an oxygen atom is present in the side chain of the IL (Table 9).

TABLE 9

Results from reactions using solvent 2 (KG51)

| Solvent | Experiment (E)/ Recycle (R) | Time (h) | % Conversion | % Selectivity Product 8 |
|---|---|---|---|---|
| (KG51) | E1 | 48 | 100 | 93$^a$ |

$^a$Isolated yield = 87%

Upon increasing the number of oxygen atoms in the IL side chain from one to two, the selectivity is only slightly negatively affected. There is however a significant drop in conversion by the 3$^{rd}$ recycle (to 64%) (Table 10).

TABLE 10

Results from reactions using solvent 6 (KG55)

| Solvent | Experiment (E)/ Recycle (R) | Time (h) | % Conversion | % Selectivity Product 8 |
|---|---|---|---|---|
| (KG55) | E1 | 24 | 32 | 100 |
|  |  | 48 | 97 | 88$^a$ |
|  | R1 | 24 | 100 | 100 |
|  |  | 48 | 100 | 88 |
|  | R2 | 24 | 31 | 100 |
|  |  | 48 | 85 | 91 |
|  | R3 | 24 | 34 | 90 |
|  |  | 48 | 64 | 93 |

$^a$isolated yield = 77%

In order to compare the reactions in commercially available solvents, including a commercially available IL, trans cinnamaldehyde was hydrogenated using [bmim][NTf$_2$], [bmim][OctOSO$_3$] or toluene. The results obtained (Table 11), show selectivity in these commercially available ILs is merely comparable to a volatile organic solvent (toluene).

TABLE 11

Hydrogenation of trans cinnamaldehyde with commercially available solvents

| Solvent | Experiment (E)/ Recycle (R) | Time (h) | % Conversion | % Selectivity Product 8 |
|---|---|---|---|---|
| Bmim NTf$_2$ | E1 | 24 | 100 | 87 |
| Bmim OctOSO$_3$ | E1 | 24 | 100 | 69 |
| Toluene | E1 | 24 | 100 | 67 | trans-(4-hydroxy-3-methoxy)cinnamaldehyde

Demonstrating the further versatility of this process, the aldehyde trans-(4-hydroxy-3-methoxy)cinnamaldehyde was reduced to the corresponding 4-hydroxy-3-methoxy-dihydrocinnamaldehyde derivative (1,4-reduction) in 100% conversion and with 90% selectivity over the undesired product of over-reduction to the alcohol (both 1,2 and 1,4-reduction). This compares favourably with reduction in BmimNTf$_2$, a conventional ionic liquid in which only 74% selectivity is achieved (Table 12).

TABLE 12

Results from reactions using solvent 1 (KG48)

| Solvent | Time (h) | % Conversion | % Selectivity Product 8 |
|---|---|---|---|
| (KG48) | 48 | 100 | 90 |
| BmimNTf$_2$ | 48 | 100 | 74 |

Benzyl Cinnamate

In order to achieve the selective hydrogenation of the olefin moiety of benzyl cinnamate without hydrogenolysis of the benzyl ester, elaborate conditions are often required (23).

The effect of catalyst loading, as well as the solvent effect was investigated during hydrogenations of benzyl cinnamate using a number of ILs of the invention, along with a number of commercially available solvents (Table 13).

TABLE 13

Effect of Catalyst Loading

| Solvent | Cat. Loading (g) | Time (h) | % Conversion | % Selectivity 12 |
|---|---|---|---|---|
| (KG48) | 0.01 | 24 | 100 | 0 |
|  | 0.005 | 24 | 100 | 0 |
| (KG51) | 0.01 | 24 | 100 | 0 |
|  | 0.005 | 24 | 100 | 100 |
|  | 0.005 | 24 | 100 | 100 |
|  | 0.005 | 48 | 100 | 100 |
|  | 0.0025 | 24 | 32 | 100 |
| (KG35) | 0.01 | 24 | 100 | 53 |
|  | 0.005 | 24 | 10 | 100 |
|  | 0.0025 | 24 | 5 | 100 |
|  | 0.005 | 48 | 19 | 100 |
|  | 0.0025 | 48 | 0 | 0 |
| (KG38) | 0.005 | 24 | 100 | 100 |
|  | 0.01 | 48 | 100 | 56 |
|  | 0.005 | 48 | 11 | 100 |
|  | 0.0025 | 48 | 0 | 0 |
| Bmim NTf$_2$ | 0.005 | 24 | 100 | 0 |
| Bmim OctOSO$_3$ | 0.005 | 24 | 100 | 0 |
| THF | 0.005 | 24 | 100 | 0 |
| Ethyl acetate | 0.005 | 24 | 100 | 0 |
| methanol | 0.005 | 24 | 100 | 0 |

The least amount of catalyst effective in inducing 100% conversion was 0.005 g. Using half this value, only 32% conversion was achieved after 24 h with IL (KG51). The octylsulfate ILs ((KG35) and (KG38)) gave promising results in terms of selectivity; however this was only achieved when conversion was low for IL(KG35), but with optimal conversion for IL (KG38). The most compelling results from this data set are obtained using ILs (KG51) and (KG38). Using 0.005 g catalyst, after 24 h, 100% conversion and selectivity were obtained. More surprising is the fact that the selectivity was retained up to 48 h, thus suggesting that hydrogenolysis of this compound in this IL system only occurs with the unsaturated ester. More evidence of this fact is observed when the non-hydrogenolysed reduced product (12) is further subjected to hydrogenation conditions using an increased amount of catalyst. No hydrogenolysis is observed (Table 14). The significance of this result is based on the fact that IL (KG51) completely prevents hydrogenolysis of the benzyl ester.

TABLE 14

Hydrogenation of benzyl 3-phenylpropanoate (12)

| Solvent | Cat. Loading (g) | Time (h) | % Conversion | % Selectivity Product 12 |
|---|---|---|---|---|
| (KG51) | 0.01 | 24 | 0 | 100 |

The system used to obtain 100% selectivity using IL (KG51) was recycled 4 times with no loss in activity (Table 15).

TABLE 15

Recycling of IL (KG51) system

| Solvent | Experiment (E)/ Recycle (R) | % Conversion | % Selectivity Product 12 |
|---|---|---|---|
| (KG51) | E1 | 100 | 100 |
|  | R1 | 100 | 100 |
|  | R2 | 100 | 100 |
|  | R3 | 100 | 100 |
|  | R4 | 100 | 100 |
|  | R5 | 98 | 100 |
|  | R6 | 91 | 100 |
|  | R7 | 91 | 100 |
|  | R8 | 81 | 100 |

After the fourth recycle, the selectivity remains constant, but the conversion decreases slightly to 91% upon recycle 7. Only upon recycle 8 is a significant drop in conversion observed (81%).

Varying catalytic amounts were tested for the hydrogenation of benzyl cinnamate using IL (KG38) (Table 16).

TABLE 16

Varying catalytic amount for the hydrogenation of benzyl cinnamate in IL (KG38)

| Solvent | Cat. Loading (g) | Time (h) | % conversion | % Selectivity Product 12 |
|---|---|---|---|---|
| (KG38) | 0.005 | 24 | 100 | 100 |
|  | 0.006 |  | 100 | 68 |
|  | 0.007 |  | 100 | 55 |

TABLE 16-continued

Varying catalytic amount for the hydrogenation of benzyl cinnamate in IL (KG38)

| Solvent | Cat. Loading (g) | Time (h) | % conversion | % Selectivity Product 12 |
|---|---|---|---|---|
| | 0.008 | | 100 | 26 |
| | 0.009 | | 100 | 25 |

As can be seen from the results displayed in Table 16, the increasing amount of catalyst favours hydrogenolysis, optimum conditions being observed with 0.005 g catalyst.

The effect of cation chain length and the number of oxygens in the side chain was investigated to determine whether, it was only the cation from ILs (KG51) and (KG38) that gave the best selectivity (Table 17).

TABLE 17

Effect of ILs of differing cation on the selective reduction of benzyl cinnamate

| Solvent | Cat. Loading (g) | Time (h) | % Conversion | % Selectivity Product 12 |
|---|---|---|---|---|
| (KG49) | 0.005 | 24 | 100 | 7 |
| (KG50) | | | | 0 |
| (KG52) | | | | 34 |
| (KG55) | | | | 44 |
| (neat benzyl cinnamate) | | | | 0 |

It is evident from the results obtained that any difference in the length of the side chain or the number of oxygen atoms in the chain negatively affects the selectivity of the reaction. This reaction is therefore sensitive to any changes in IL composition concerning the IL cation.

Based on the conditions from the result obtained using IL (KG51) and (KG38) and 0.005 g catalyst, this system was used to test other compounds comprising hydrogenolysable functionalities.

Allyl Cinnamate

Figure 8:
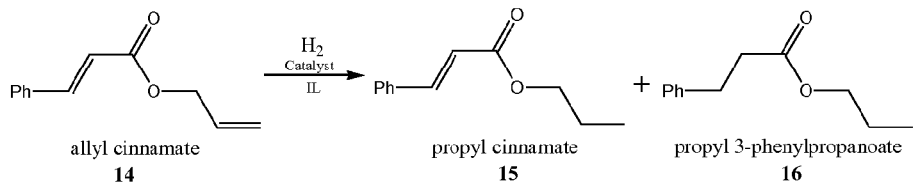
FIG. 8: Reduction of allyl cinnamate.
Figure 9:
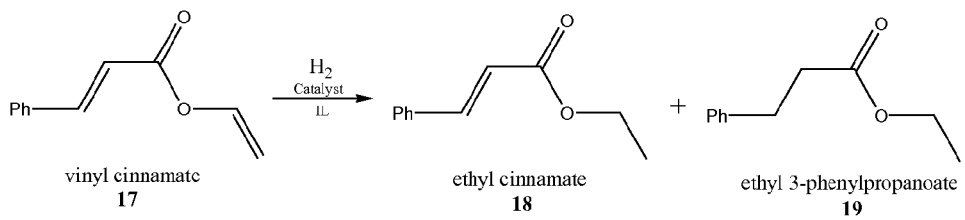
FIG. 9: Reduction of vinyl cinnamate.

The hydrogenation of allyl cinnamate can lead to the reduction either of the olefinic bonds, or even hydrogenolysis of the allyl functionality may be observed (FIG. 8).

Using both ILs, although no hydrogenolysis was observed in either the corresponding Bmim ILs nor the common organic solvent, ethyl acetate, 84% selectivity was reached using IL (KG51) (Table 18).

TABLE 18

| IL | % Conversion | % Selectivity Product 15 |
|---|---|---|
| (KG51) | 100 | 84 |
| (KG38) | 100 | 71 |
| Bmim NTf$_2$ | 100 | 0 |
| Bmim OctOSO$_3$ | 100 | 0 |
| Ethyl acetate | 100 | 0 |

Vinyl Cinnamate

Hydrogenolysis of vinyl cinnamate is more likely to occur if a platinum species is used as the catalyst (24).

A moderate 49% selectivity was obtained using the octylsulfate IL, (KG38), in comparison with no selectivity for IL (KG51) and ethyl acetate (Table 30).

TABLE 19

| IL | % Conversion | % Selectivity 18 |
|---|---|---|
| (KG51) | 100 | 0 |
| (KG38) | 100 | 49 |
| Ethyl acetate | 100 | 0 |

Experimental

Typical Procedure

10% Pd/C (5.0 mg unless otherwise stated) was weighed into a dry 2-neck round bottom flask. The pre-dried IL (2.0 mL) was then added to the flask, followed by the desired substrate (4 mmol) and 3 N$_2$/vacuum cycles were performed. 0.0012 mol % catalyst was used. The reaction mixture was allowed to stir for 10 minutes or until reaching the desired reaction temperature, or until all the substrate had dissolved in the IL. Hydrogen was then introduced to the reaction via a balloon, and the progress of the reaction was monitored by $^1$H NMR at 24 and 48 hour intervals. Quantitative analysis of the reaction products was carried out by measuring the integration ratio of the peaks from the crude NMR spectrum. These values were then often verified by purification of the product by column chromatography and thus the calculation of isolated yields. Upon termination of the reaction, the products were extracted using hexane (10×3 mL). The mass recovery after extraction from the IL was always >98%. In the case of reactions carried out in octylsulfate ILs, the product was either distilled from the IL using high vacuum or a brief column was prepared to separate product from IL. These procedures generally led to a lower mass recovery (>80%), due to product being lost on the column or lost during the distillation procedure. All reactions carried out in the NTf$_2$ ILs were carried out at 55° C. and 65° C. in the octylsulfate ILs.

Recycle Procedure

Following extraction of the products from the IL, the IL (containing the catalyst) was dried and analysed by $^1$H NMR. Following confirmation that the IL was substrate/product-free and had not degraded, fresh substrate was then added to the system and the reactions recommenced as described.

Figure 10:
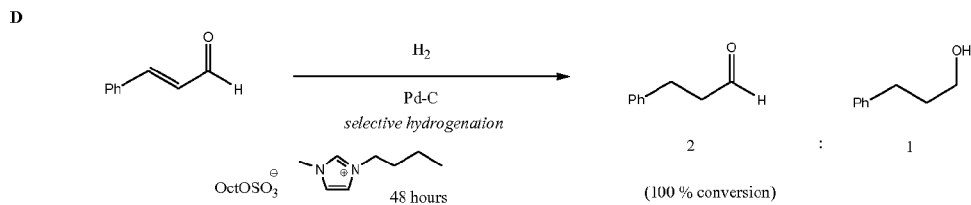
FIG. 10: Schemes D-F: Selective hydrogenation of trans-cinnamaldehyde and trans-(4-hydroxy-3-methoxy)cinnamaldehyde.
Figure 10:
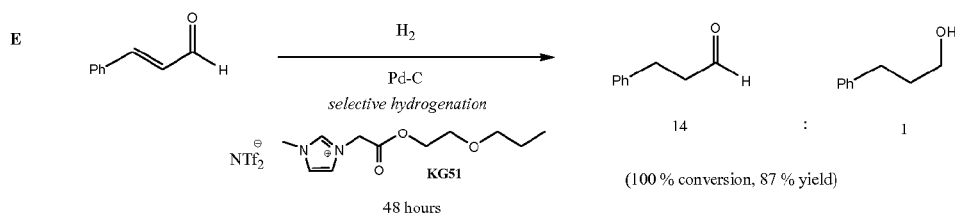
Figure 10:
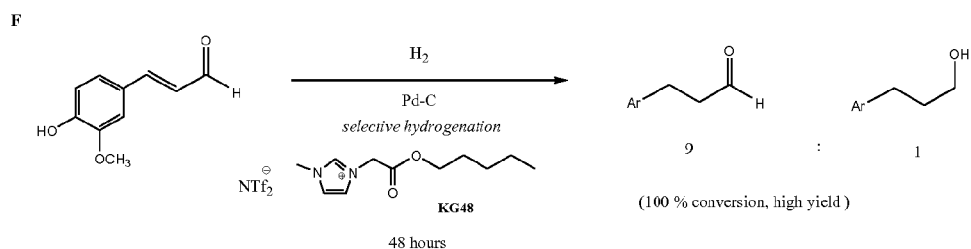
Figure 11:
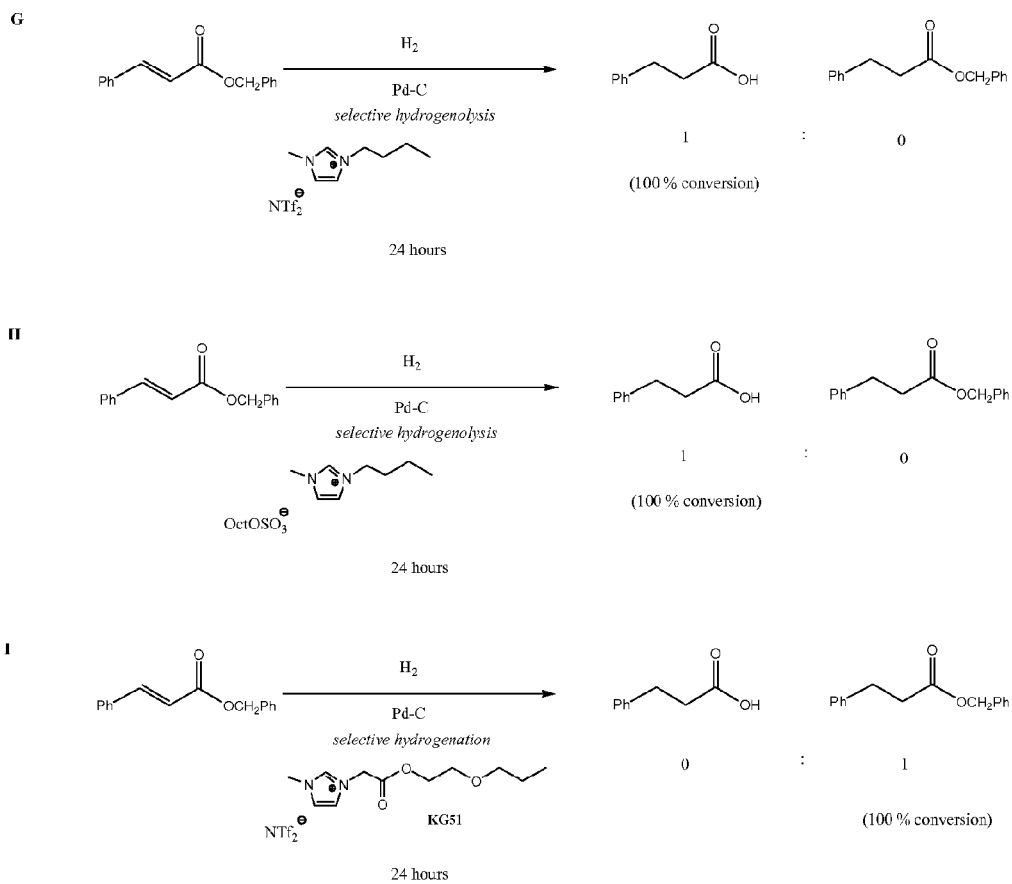
FIG. 11: Schemes G-I: Selective hydrogenation of trans-benzyl cinnamate to benzyl hydrocinnamate, avoiding hydrogenolysis of the benzyl ester group.

The use of IL KG51 as a solvent in the selective reduction of trans-cinnamaldehyde to hydrocinnamaldehyde in the presence of hydrogen gas and palladium supported on carbon as a catalyst. KG51, is preferred because of the presence of ether oxygens in the side-chain, which increase biodegradability and decrease toxicity. At the same time, the selectivity of the reduction is much higher than with conventional ILs such as 1-butyl-3-methylimidazolium octylsulfate (bmim OctOSO$_3$) (Table 11 and FIG. 10). Also the use of IL KG51 as a solvent for the selective hydrogenation of the carbon-carbon double bond conjugated to the carbonyl group in benzyl cinnamate without cleaving the benzyl ester using hydrogen gas and palladium supported on carbon as a catalyst. The use of conventional ILs such as 1-butyl-3-methylimidazolium NTf$_2$ (bmimNTf$_2$) or 1-butyl-3-methylimidazolium octylsulfate (bmim OctOSO$_3$) typically leads to hydrogenolysis of the benzyl ester, as well as hydrogenation of the carbon-carbon double bond conjugated to the carbonyl group (Table 13 and FIG. 11).

REFERENCES 1. (a) P. Wasserscheid and W. Keim, Angew. Chem., Int. Ed., 2000, 39, 3772; (b) T. Welton, Chem. Rev., 1999, 99, 2071; (c) J. D. Holbury and K. R. Seddon, Clean Prod. Process., 1999, 1, 223; (d) P. Bonhôte, A-P Dias, N. Papageorgiou, K. Kalyanasundaram and M. Grätzal, Inorg. Chem., 1996, 35, 1168; (e) R. P. Swatloski, S. K. Spear, J. D. Holbrey and R. D. Rogers, J. Am. Chem. Soc., 2002, 124, 4974-4975; (f) D. M. Phillips, L. F. Drummy, D. G. Conrady, D. M. Fox, R. R. Naik, M. O, Stone, P. C. Trulove, H. C. De Long and R. A. Mantz, J. Am. Chem. Soc., 2004, 126, 14350-14351; (g) Q. Liu, M. H. A. Janssen, F. van Rantwijk and R. A. Sheldon, Green Chem., 2005, 7, 39-42; (h) H. Xie, S. Li and S. Zhang, Green Chem., 2005, 7, 606-608; (i) J. D. Holbrey, S. K. Spear, M. B. Turner, R. P. Swatloski and R. D. Rogers, U.S. Pat. No. 6,808,557, 2004; (j) M. B. Turner, S. K. Spear, J. D. Holbrey and R. D. Rogers, Biomacromolecules, 2004, 5, 1379-1384; (k) M. B. Turner, S. K. Spear, J. D. Holbrey, D. T. Daly and R. D. Rogers, Biomacromolecules, 2005, 6, 2497-2502.
2. (a) J. G. Huddleston, H. D. Willauer, R. P. Swatloski, A. E. Visser and R. D. Rogers, Chem. Commun., 1998, 1765; (b) L. Blanchard, D. Nancu, E. J. Bechman and J. F. Bennecke, Nature, 1999, 399, 28; (c) A. E. Visser, R. P. Swatloski, W. M. Reichert, S. T. Griffin and R. D. Rogers, Ind. Eng. Chem. Res., 2000, 39, 3596.
3. (a) P. J. Scammells, N. Gathergood and J. Ripper, PCT Int. Appl., 2002, 25 pp. WO 0216367; (b) I. Hemeon, N. W. Barnett, N. Gathergood, P. J. Scammells and R. D. Singer, Aust. J. Chem., 2004, 2, 125.
4. R. Sheldon, Chem. Commun., 2001, 23, 2399.
5. (a) W. M. Nelson, Ionic liquids: industrial applications for green chemistry, ACS Symp. Ser. 818, ed. R. D. Rogers and K. R. Seddon, 2002, pp. 30-41; (b) T. Laird, S. A. Hermitage and U. Tilstam, Org. Process Res. Dev., 2002, 6, 338; (c) R. P. Swatloski, J. D. Holbrey and R. D. Rogers, Green Chem., 2003, 5, 361.
6. M. J. Scott and M. N. Jones, Biochim. Biophys. Acta, 2000, 1508(1-2), 235.
7. (a) R. Freer and A. Curzon, NATO Sci. Ser. II: Math. Phys. Chem., 2003, 92, 129; (b) J. D. Holbury, Ionic liquids: industrial applications for green chemistry, ACS Symp. Ser. 818, ed. R. D. Rogers and K. R. Seddon, 2002, pp. 446-4458.
8. K. R. Seddon, Nat. Mater., 2003, 2(6), 363. In this efficient case methyl imidazole is converted to the ionic liquid (the hydrochloride salt of methyl imidazole), then the methyl imidazole is regenerated and recycled.
9. (a) N. Bodor, J. J. Kaminski and S. Selk, J. Med. Chem., 1980, 23(5), 469; (b) N. Bodor and J. J. Kaminski, J. Med. Chem., 1980, 23(5), 566; (c) Bodor, R. Woods, C. Raper, P. Kearney and J. J. Kaminski, J. Med. Chem., 1980, 23(5), 474; (d) N. Bodor 1976 U.S. Pat. No. 3,989,7111; (e) N. Bodor, 1979 U.S. Pat. No. 4,160,099.
10. (a) R. S. Boethling, Designing Safer Chemicals, ACS Symp. Ser. 640, 1996, 156; (b) P. H. Howard, R. S. Boethling, W. Stiteler, W. Meylan and J. Beauman, Sci. Total Environ., 1991, 109/110, 635; (c) R. S. Boethling, Cationic Surfactants, Surfactant Science Series Vol. 53, Marcel Dekker, New York, 1994, pp. 95-135
11. (a) N. Gathergood and P. J. Scammells, Aust. J. Chem., 2002, 55, 557; (b) M. Teresa Garcia, N. Gathergood and P. J. Scammells Green Chemistry, 2004, 166-175 (c) M. Teresa Garcia, N. Gathergood and P. J. Scammells Green Chemistry, 2005, 9-14, (d) M. Teresa Garcia, N. Gathergood and P. J. Scammells Green Chemistry 2006 156-160.
12. B. Jastorff, R. Störmann, J. Ranke, K. Mölter, F. Stock, B. Oberheitmann, W. Hoffmann, J. Hoffmann, M. Nüchter, B. Ondruschka and J. Filser, Green Chem., 2003, 5, 136.
13. OECD Chemical Group, Ready Biodegradability: Closed Bottle Test. Method 301 D, OECD Revised Guidelines for Tests for Ready Biodegradability, Paris, France, 1993.
14. ISO 14593: Water quality. Evaluation of ultimate aerobic biodegradability of organic compounds in aqueous medium. Method by analysis of inorganic carbon in sealed vessels ($CO_2$ headspace test), 1999.
15. (a) Y. Kume, K. Qiao, D. Tomida and C. Yokoyama, Catalysis Communications, 2008, 9, 369; (b) Y. Kanazawa and H. Nishiyama, Synlett, 2006, 19, 3343; (c) F. Lopez-Linares, G. Agrifolio, A. Labrador and A. Karam, Journal of Molecular Catalysis A, 2004, 207, 115; (d) A. Mori, T. Mizusaki, Y. Miyakawa, E. Ohashi, T. Haga, T. Maegawa, Y. Monguchi and H. Sajiki, Tetrahedron, 2006, 62, 11925; (e) T. Ikawa, H. Sajiki and K. Hirota, Tetrahedron, 2005, 61, 2217.
16. (a) A. Wolfson, I. Vankelecom and P. Jacobs, Tetrahedron Letters, 2005, 46, 2513; (b) A. Z. P. Suarez, E. L. J. Dullius, S. Einloft, F. Roberto de Souza, and J. Dupont, Inorganica Chimica Acta, 1997, 255, 207; (c) T. Suarez, B. Fontal, M. Reyes, F. Bellandi, R. Contreras, J. Ortega, G. Leon, P. Cancines and B. Castillo, *React. Kinet. Catal. Lett.*, 2004, 82, 325; (d) D. Zhao, P. Dyson, G. Laurenczy and S. McIndoe, *Journal of Molecular Catalysis A*, 2004, 214, 19.
17. (a) Boxwell, P. Dyson, D. Ellis and T. Welton, J. Am. Chem. Soc, 2002, 124, 9334.; (b) Dupont, G. Fonseca, A. Umpierre, P. Fichtner and S. Teixeira, J. Am. Chem. Soc., 2002, 124, 4228.
18. (a) P. Dyson, D. Ellis, W. Henderson and G. Laurenczy, Adv. Synth. Catal., 2003, 345.; (b) P. Dyson, G. Laurenczy, C. Andre Ohlin, J. Valiance and T. Welton, Chem. Commun., 2003, 2418; (c) L. Rossi, G. Machado, P. fichtner, S. Teixeira and J. Dupont, Catalysis Letters, 2004, 92 (3-4), 149-255; (d) M. Steffan, M. Lucas, A. Brandner, M. Wollny, N. Oldenburg and P. Claus, Chem. Eng. Technol., 2007, 30, 481; (d) K. Anderson, P. Goodrich, C. Hardacre and D. Rooney, Green Chemistry, 2003, 5, 448.
19. H. Zhaol, G. A. Baker, Z. Song, O. Olubajo, T. Crittle, and D. Peters, Green Chem., 2008, 10, 696-705.
20. V. K. Yadav and K. G. Babu, J. Org. Chem., 2004, 69, 577-580.
21. APHA (American Public Health Association), AWWA (American Water Works Association), and WPCF (Water Pollution Control Federation), Method 508 B, Standard Methods for the Examination of Water and Wastewater, Washington, 16th edn, 1985, pp. 532-537.
22. (a) F. Benvenuti, C. Carlini, M. Marchionna, A. M. Galletti and G. Sbrana, *Journal of Molecular Catalysis A*, 1999, 145, 221. (b) Y. Kume, K. Qiao, D. Tomida and C. Yokoyama, *Catalysis Communications*, 2008, 9, 369; (c) Y. Kanazawa and H. Nishiyama, *Synlett*, 2006, 19, 3343; (d) F. Lopez-Linares, G. Agrifoglio, A. Labrador and A. Karam, *Journal of Molecular Catalysis A*, 2004, 207, 115; (e) Y. Zhang, S. Liao, Y. Xu and D. Yu, *Applied Catalysis A*, 2000, 192, 247.
23. (a) A. Mori, T. Mizusaki, Y. Miyakawa, E. Ohashi, T. Haga, T. Maegawa, Y. Monguchi and H. Sajiki, Tetrahedron, 2006, 62, 11925; (b) J. Le Bras, D. K. Mukherjee, S. Gonzalez, M. Tristany, B. Ganchegui, M. Moreno-Manas, R. Pleixats, F. Henin and J. Muzart, New J. Chem., 2004, 28, 1550; (c) H. Sajiki, T. Ikawa and K. Hirota, Tetrahedron Letters, 2003, 44, 8437; (d) T. Ikawa, H. Sajiki and K. Hirota, Tetrahedron, 2005, 61, 2217; (e) D. Belotti, G.

Cantagrel, C. Combellas, J. Cossy, F. Kanoufi and S, Nunige, New J. Chem., 2005, 29, 761

24. In Hydrogenation Methods (Best Synthetic Methods), London; Orlando [Fla.]: Academic Press, 1985; Paul Nels Rylander, p. 165.

The invention claimed is:

1. A compound consisting of an alkyl substituted imidazolium cationic core and an associated counter anion, wherein the imidazolium cationic core has a —C=OX— side chain in the 3-position of the imidazole ring, the —C=OX— side chain comprising a straight alkyl chain and at least one ether linkage, wherein X=O or S.

2. The compound according to claim 1 wherein X is O and the —C=OX— side chain comprises an ester group.

3. The compound according to claim 1 wherein the alkyl chain comprises from 4 to 13 atoms.

4. The compound according to claim 1 wherein X is S and the —C=OX— side chain comprises a thioester group.

5. The compound according to claim 1 characterized in that the imidazole ring is substituted with at least one $C_1$-$C_4$ alkyl group.

6. The compound according to claim 1 characterized in that the imidazole ring is substituted in at least one position with at least one alkyl group selected from the group consisting of 1-methyl, 2-methyl, 4-methyl, 5-methyl, 1-ethyl, 2-ethyl, 4-ethyl, 5-ethyl, 1-propyl, 2-propyl, 4-propyl, 5-propyl and 4-trifluoromethyl.

7. The compound according to claim 1 characterized in that the —C=OX— side chain comprises 1-4 ether linkages.

8. The compound according to claim 1 characterized in that the —C=OX— side chain is selected from the group consisting of 2-methoxyethyl ester, 2-ethoxyethyl ester, 2-propoxyethyl ester, 2-butoxyethyl ester, 2-(2-ethoxyethoxy)ethyl ester, 2-(2-propoxyethoxy)ethyl ester and 2-(2-butoxyethoxy)ethyl ester, 2-[2-(2-methoxyethoxy)ethoxy]ethyl ester, 2-[2-(2-ethoxyethoxy)ethoxy]ethyl ester, 2-[2-(2-propoxyethoxy)ethoxy]ethyl ester and 2-[2-(2-butoxyethoxy)ethoxy]ethyl ester.

9. The compound according to claim 1 characterized in that the —C=OX— side chain is selected from the group consisting of 2-methoxyethyl thioester, 2-ethoxyethyl thioester, 2-propoxyethyl thioester, 2-butoxyethyl thioester, 2-(2-ethoxyethoxy)ethyl thioester, 2-(2-propoxyethoxy)ethyl thioester and 2-(2-butoxyethoxy)ethyl thioester, 2-[2-(2-methoxyethoxy)ethoxy]ethyl thioester, 2-[2-(2-ethoxyethoxy)ethoxy]ethyl thioester, 2-[2-(2-propoxyethoxy)ethoxy]ethyl thioester and 2-[2-(2-butoxyethoxy)ethoxy]ethyl thioester.

10. The compound according to claim 1 characterized in that the counter anion is selected from the group consisting of $Br^-$, $Cl^-$, $I^-$, $NTf_2^-$, $BF_4^-$, $PF_6^-$, $N(CN)_2^-$, sulfate, $OctOSO_3^-$, tosylate, benzenesulfonate, hydrogen sulfate, a linear alkyl sulfate, heptadecafluorooctanesulfonate, 2-(2-methoxyethoxy)-ethylsulfate, methanesulfonate, trifluoromethanesulfonate, nonafluorobutanesulfonate, phosphate, dimethyl phosphate, diethyl phosphate, bis(pentafluoroethyl)phosphinate, bis(2,4,4-trimethylpentyl)-phosphinate, tris(pentafluoroethyl)trifluorophosphate, tris(heptafluoropropyl)trifluorophosphate, tris(nonafluorobutyl)trifluorophosphate, diethylphosphate, nitrate, thiocyanate, tricyanomethanide, bis(pentafluoroethylsulfonyl)imide, bis(trifluoromethyl)imide, tris(trifluoromethylsulfonyl)methide, bis(methanesulfonyl)amide, 2,2,2-trifluoro-N-(trifluoromethylsulfonyl)acetamide and tetracyanoborate, bis[oxalato]borate, bis-[1,2-benzenediolato(2-)]borate, bis-[salicylato(2-)]borate, bis-[malonato(2-)]-borate, bis-[2,2'biphenyl-diolato-(2-)-O,O']-borate, acetate, trifluoroacetate, decanoate, hexafluoroantimonate, tetrachloroaluminate and cobalt tetracarbonyl.

11. The compound according to claim 10 wherein the linear alkyl sulfate has general formula $C_nH_{2n+1}OSO_3^-$, n=1 to 8, and is selected from the group consisting of methyl sulfate, ethyl sulfate, propyl sulfate, butyl sulfate, pentyl sulfate, hexyl sulfate, heptyl sulphate, octyl sulfate and trifluoroethyl sulfate.

12. The compound according to claim 1, characterized in that the counter anion is $OctOSO_3^-$.

13. A compound selected from the group consisting of

KG7 (3-methyl-1-(2-[2-methoxy]ethoxycarbonylmethyl)imidazolium bromide),

KG8 (3-methyl-1-(2-[2-ethoxy]ethoxycarbonylmethyl)imidazolium bromide),

KG9 (3-methyl-1-(2-[2-propoxy]ethoxycarbonylmethyl)imidazolium bromide),

KG10 (3-methyl-1-(2-[2-butoxy]ethoxycarbonylmethyl)imidazolium bromide),

KG12 (3-methyl-1-(2-[2-methoxyethoxy]ethoxycarbonylmethyl)imidazolium bromide),

KG13 (3-methyl-1-(2-[2-ethoxyethoxy]ethoxycarbonylmethyl)imidazolium bromide),

KG14 (3-methyl-1-(2-[2-propoxyethoxy]ethoxycarbonylmethyl)imidazolium bromide),

KG15 (3-methyl-1-(2-[2-butoxyethoxy]ethoxycarbonylmethyl)imidazolium bromide),

KG16 (2,3-dimethyl-1-(2-[2-butoxy]ethoxycarbonylmethyl)imidazolium bromide),

KG18 (2,3-dimethyl-1-(2-[2-methoxyethoxy]ethoxycarbonylmethyl)imidazolium bromide), KG23 (3-methyl-1-(2-[2-methoxy]ethoxycarbonylmethyl)imidazolium $PF_6$), KG24 (3-methyl-1-(2-[2-ethoxy]ethoxycarbonylmethyl)imidazolium $PF_6$), KG25 (3-methyl-1-(2-[2-propoxy]ethoxycarbonylmethyl)imidazolium $PF_6$), KG26 (3-methyl-1-(2-[2-butoxy]ethoxycarbonylmethyl)imidazolium $PF_6$), KG27 (3-methyl-1-(2-[2-methoxyethoxy]ethoxycarbonylmethyl)imidazolium $PF_6$), KG28 (3-methyl-1-(2-[2-ethoxyethoxy]ethoxycarbonylmethyl)imidazolium $PF_6$), KG29 (3-methyl-1-(2-[2-propoxyethoxy]ethoxycarbonylmethyl)imidazolium $PF_6$), KG30 (3-methyl-1-(2-[2-butoxyethoxy]ethoxycarbonylmethyl)imidazolium $PF_6$), KG32 (2,3-dimethyl-1-(2-[2-butoxy]ethoxycarbonylmethyl)imidazolium $PF_6$), KG33 (2,3-dimethyl-1-(2-[2-methoxyethoxy]ethoxycarbonylmethyl)imidazolium $PF_6$), KG34 (3-methyl-1-(butoxycarbonylmethyl)imidazolium octylsulfate), KG35 (3-methyl-1-(pentoxycarbonylmethyl)imidazolium octylsulfate), KG36 (3-methyl-1-(2-[2-methoxy]ethoxycarbonylmethyl)imidazolium octylsulfate), KG37 (3-methyl-1-(2-[2-ethoxy]ethoxycarbonylmethyl)imidazolium octylsulfate), KG38 (3-methyl-1-(2-[2-propoxy]ethoxycarbonylmethyl)imidazolium octylsulfate), KG39 (3-methyl-1-(2-[2-butoxy]ethoxycarbonylmethyl)imidazolium octylsulfate), KG40 (3-methyl-1-(2-[2-methoxyethoxy]ethoxycarbonylmethyl)imidazolium octylsulfate), KG41 (3-methyl-1-(2-[2-ethoxyethoxy]ethoxycarbonylmethyl)imidazolium octylsulfate),
KG42 (3-methyl-1-(2-[2-propoxyethoxy]ethoxycarbonylmethyl)imidazolium octylsulfate),
KG43 (3-methyl-1-(2-[2-butoxyethoxy]ethoxycarbonylmethyl)imidazolium octylsulfate),
KG44 (2,3-dimethyl-1-(2-[2-butoxy]ethoxycarbonylmethyl)imidazolium octylsulfate),
KG45 (2,3-dimethyl-1-(2-[2-methoxyethoxy]ethoxycarbonylmethyl)imidazolium octylsulfate,
KG49 (3-methyl-1-(2-[2-methoxy]ethoxycarbonylmethyl)imidazolium $NTf_2$),
KG50 (3-methyl-1-(2-[2-ethoxy]ethoxycarbonylmethyl)imidazolium $NTf_2$),
KG51 (3-methyl-1-(2-[2-propoxy]ethoxycarbonylmethyl)imidazolium $NTf_2$),
KG52 (3-methyl-1-(2-[2-butoxy]ethoxycarbonylmethyl)imidazolium $NTf_2$),
KG53 (3-methyl-1-(2-[2-methoxyethoxy]ethoxycarbonylmethyl)imidazolium $NTf_2$),
KG54 (3-methyl-1-(2-[2-ethoxyethoxy]ethoxycarbonylmethyl)imidazolium $NTf_2$),
KG55 (3-methyl-1-(2-[2-propoxyethoxy]ethoxycarbonylmethyl)imidazolium $NTf_2$),
KG56 (3-methyl-1-(2-[2-butoxyethoxy]ethoxycarbonylmethyl)imidazolium $NTf_2$),
KG58 (2,3-dimethyl-1-(2-[2-butoxy]ethoxycarbonylmethyl)imidazolium $NTf_2$),
KG59 (2,3-dimethyl-1-(2-[2-methoxyethoxy]ethoxycarbonylmethyl)imidazolium $NTf_2$),
KG62 (3-methyl-1-(2-[2-methoxy]ethoxycarbonylmethyl)imidazolium $BF_4$),
KG63 (3-methyl-1-(2-[2-ethoxy]ethoxycarbonylmethyl)imidazolium $BF_4$),
KG64 (3-methyl-1-(2-[2-propoxy]ethoxycarbonylmethyl)imidazolium $BF_4$),
KG65 (3-methyl-1-(2-[2-butoxy]ethoxycarbonylmethyl)imidazolium $BF_4$),
KG66 (3-methyl-1-(2-[2-methoxyethoxy]ethoxycarbonylmethyl)imidazolium $BF_4$),
KG67 (3-methyl-1-(2-[2-ethoxyethoxy]ethoxycarbonylmethyl)imidazolium $BF_4$),
KG68 (3-methyl-1-(2-[2-propoxyethoxy]ethoxycarbonylmethyl)imidazolium $BF_4$),
KG69 (3-methyl-1-(2-[2-butoxyethoxy]ethoxycarbonylmethyl)imidazolium $BF_4$),
KG71 (2,3-dimethyl-1-(2-[2-butoxy]ethoxycarbonylmethyl)imidazolium $BF_4$),
KG72 (2,3-dimethyl-1-(2-[2-methoxyethoxy]ethoxycarbonylmethyl)imidazolium $BF_4$),
KG75 (3-methyl-1-(2-[2-methoxy]ethoxycarbonylmethyl)imidazolium $N(CN)_2$),
KG76 (3-methyl-1-(2-[2-ethoxy]ethoxycarbonylmethyl)imidazolium $N(CN)_2$),
KG77 (3-methyl-1-(2-[2-propoxy]ethoxycarbonylmethyl)imidazolium $N(CN)_2$),
KG78 (3-methyl-1-(2-[2-butoxy]ethoxycarbonylmethyl)imidazolium $N(CN)_2$),
KG79 (3-methyl-1-(2-[2-methoxyethoxy]ethoxycarbonylmethyl)imidazolium $N(CN)_2$),
KG80 (3-methyl-1-(2-[2-ethoxyethoxy]ethoxycarbonylmethyl)imidazolium $N(CN)_2$),
KG81 (3-methyl-1-(2-[2-propoxyethoxy]ethoxycarbonylmethyl)imidazolium $N(CN)_2$),
KG82 (3-methyl-1-(2-[2-butoxyethoxy]ethoxycarbonylmethyl)imidazolium $N(CN)_2$),
KG84 (2,3-dimethyl-1-(2-[2-butoxy]ethoxycarbonylmethyl)imidazolium $N(CN)_2$),
KG85 (2,3-dimethyl-1-(2-[2-methoxyethoxy]ethoxycarbonylmethyl)imidazolium $N(CN)_2$),
KG405 (3-methyl-1-[bis-1-methoxyethyl]carbamylmethyl)imidazolium octylsulfate) and
KG407 (3-methyl-1-[bis-1-methoxyethyl]carbamylmethyl)imidazolium bromide)
KG422 (3-methyl-1-[1-methoxyethyl]carbamylmethyl)imidazolium bromide),
KG423 (3-methyl-1-[1-methoxypropyl]carbamylmethyl)imidazolium bromide).

14. A method of preparing the compound according to claim 1 or 13 comprising the steps of:
forming a halo ester alkylating agent by reacting an alcohol comprising an ether or polyether group with halo acetyl halide; and
reacting said halo ester alkylating agent with an imidazole to form an imidazole ester halide salt.

15. The method as claimed in claim 14 wherein the halo acetyl halide is selected from the group consisting of bromo acetyl bromide, chloro acetyl chloride, bromo acetyl chloride and chloro acetyl bromide.

16. The method according to claim 14 wherein the halide salt is reacted with an alkali salt in an anion exchange reaction, the alkali salt comprising an $NTf_2^-$, $BF_4^-$, $PF_6^-$, $N(CN)_2^-$, or an $OctOSO_3^-$ anion.

17. The method according to claim 14 wherein the compound comprises an ether linkage containing chain which is selected from the group consisting of 2-methoxyethyl ester, 2-ethoxyethyl ester, 2-propoxyethyl ester, 2-butoxyethyl ester, 2-(2-ethoxyethoxy)ethyl ester, 2-(2-propoxyethoxy)ethyl ester and 2-(2-butoxyethoxy)ethyl ester, 2-[2-(2-methoxyethoxy)ethoxy]ethyl ester, 2-[2-(2-ethoxyethoxy)ethoxy]ethyl ester, 2-[2-(2-propoxyethoxy)ethoxy]ethyl ester, 2-[2-(2-butoxyethoxy)ethoxy]ethyl ester.

18. A method of improving the biodegradability or reducing the toxicity of an imidazole cation containing ionic liquid wherein the imidazole cation comprises an ester or thioester side chain at the 3-position of the imidazole ring, the side chain comprising a straight chain alkyl group, the method comprising the step of introducing at least one ether group into the side chain.

19. The method as claimed in claim 18 further comprising the step of introducing an $OctOSO_3^-$ anion into the ionic liquid.

20. A method of reducing toxicity and/or increasing biodegradability of a chemical reaction, a biomass dissolution or a biofuel preparation, the method comprising the step of using the compound as claimed in claim 1 or 13 as a solvent or co-solvent, wherein the chemical reaction is selected from the group consisting of enzymatic and biocatalytic reactions, neutralizations, acidifications, basifications, oxidations, reductions, hydrogenation reactions, radical reactions, electrophilic additions, electrophilic substitutions, nucleophilic additions, nucleophilic substitutions, rearrangements, pericyclic reactions, and metathesis reactions.

21. The method according to claim 20 wherein the biomass dissolution is a cellulose dilution.

22. The method according to claim 20 wherein the chemical reaction is a hydrogenation reaction.

23. The method according to claim 20 wherein the chemical reaction is a metathesis reaction.

24. The method according to claim 20 wherein the chemical reaction is a pericyclic reaction.

25. The method according to claim 22 wherein the hydrogenation reaction is selective reduction of trans-cinnamaldehyde to hydrocinnamaldehyde in the presence of hydrogen gas and palladium supported on carbon.

26. The method according to claim 22 wherein the hydrogenation reaction is selective reduction of the alkene bond conjugated to the carbonyl group of benzyl cinnamate using hydrogen gas and palladium supported on carbon.

27. The method according to claim 20 wherein the compound is 3-methyl-1-(2-[2-propoxy]ethoxycarbonylmethyl) imidazolium $NTf_2$.

28. A method of preparing the compound of claim 1 or 13 comprising the steps of:
   forming a halo thioester alkylating agent by reacting a thiol comprising an ether or polyether group with halo acetyl halide; and
   reacting said halo thioester alkylating agent with an imidazole to form an imidazole thioester halide salt.

29. The method of claim 28, wherein the halo acetyl halide is selected from the group consisting of bromo acetyl bromide, chloro acetyl chloride, bromo acetyl chloride and chloro acetyl bromide.

30. The method of claim 28, wherein the halide salt is reacted with an alkali salt in an anion exchange reaction, the alkali salt comprising an $NTf_2^-$, $BF_4^-$, $PF_6^-$, $N(CN)_2^-$, or an $OctOSO_3^-$ anion.

31. The method of claim 28, wherein the compound comprises an ether linkage containing chain which is selected from the group consisting of 2-methoxyethyl thioester, 2-ethoxyethyl thioester, 2-propoxyethyl thioester, 2-butoxyethyl thioester, 2-(2-ethoxyethoxy)ethyl thioester, 2-(2-propoxyethoxy)ethyl thioester, 2-(2-butoxyethoxy)ethyl thioester, 2-[2-(2-methoxyethoxy)ethoxy]ethyl thioester, 2-[2-(2-ethoxyethoxy)ethoxy]ethyl thioester, 2-[2-(2-propoxyethoxy)ethoxy]ethyl thioester and 2-[2-(2-butoxyethoxy)ethoxy]ethyl thioester.

* * * * *